United States Patent
Cheung et al.

(10) Patent No.: US 7,459,455 B2
(45) Date of Patent: Dec. 2, 2008

(54) PYRIMIDINE COMPOUNDS

(75) Inventors: Mui Cheung, Durham, NC (US); Kristen Elizabeth Nailor, Durham, NC (US); Douglas McCord Sammond, Durham, NC (US); James Marvin Veal, Apex, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 568 days.

(21) Appl. No.: 10/503,874

(22) PCT Filed: Feb. 7, 2003

(86) PCT No.: PCT/US03/03816

§ 371 (c)(1),
(2), (4) Date: Aug. 6, 2004

(87) PCT Pub. No.: WO03/066601

PCT Pub. Date: Aug. 14, 2003

(65) Prior Publication Data

US 2005/0085637 A1    Apr. 21, 2005

Related U.S. Application Data

(60) Provisional application No. 60/355,046, filed on Feb. 8, 2002.

(51) Int. Cl.
*C07D 239/48* (2006.01)
*A61K 31/505* (2006.01)

(52) U.S. Cl. .................. 514/252.14; 514/275; 544/295; 544/323

(58) Field of Classification Search ................ 544/295, 544/323; 514/252.14, 275
See application file for complete search history.

(56) References Cited

U.S. PATENT DOCUMENTS 5,691,364 A    11/1997    Buckman et al.
7,060,827 B2 *  6/2006    Singh et al. ................. 544/323

FOREIGN PATENT DOCUMENTS

| WO | 96/28427 | 9/1996 |
|----|----------|--------|
| WO | 97/19065 | 5/1997 |
| WO | 00/12485 | 3/2000 |
| WO | 00/39101 | 7/2000 |
| WO | 00/76980 | 12/2000 |
| WO | 00/78731 | 12/2000 |
| WO | 01/60816 | 8/2001 |
| WO | 01/64654 | 9/2001 |

OTHER PUBLICATIONS

Simone, Oncology: Introduction, Cecil Textbook of Medicine, 20th Edition, vol. 1, pp. 1004-1010, 1996.*
Traxler, Protein Tyrosine Kinase Inhibitors in cancer treatment, Expert Opinion on Therapeutic Patents, 7(6):571-588, 1997.*
West, Solid Solutions, Solid state chemistry and it's applications, Wiley, New York, pp. 358 and 365, 1988.*
Vippagunta et al., Crystalline solids, Advanced Drug Delivery Reviews, 48 (2001), pp. 3-26, 2001.*
Ulrich, Crystallization, Kirk-Othmer Encyclopedia of Chemical Technology, vol. 8, pp. 113-120, (http://www.mrw.interscience.wiley.com/kirk/articles/crysrous.a01/sect4-fs.html) Aug. 2002.*
Ballara et al., PubMed Abstract (Int J Exp Pathol. 80(5):235-50) Oct. 1999.*
Shepherd, Angiogenesis inhibitors in the treatment of lung cancer, Lung Cancer 34, pp. S81-S89, 2001.*
Duda et al., VEGF-targeted cancer therapy strategies: current progress, hurdles and future prospects, Trends in Molecular Medicine, vol. 13, No. 6, pp. 223-230, Apr. 2007.*

* cited by examiner

*Primary Examiner*—Deepak Rao
(74) *Attorney, Agent, or Firm*—John L. Lemanowicz

(57) ABSTRACT

Pyrimidine derivatives, which are useful as TIE-2 and/or VEGFR-2 inhibitors are described herein. The described invention also includes methods of making such pyrimidine derivatives as well as methods of using the same in the treatment of hyperproliferative diseases.

22 Claims, No Drawings

PYRIMIDINE COMPOUNDS

This application is filed pursuant to 35 U.S.C. § 371 as a U.S. National Phase Application of International Application No. PCT/US03/03816 filed Feb. 7, 2003, which claims priority from US 60/355,046 filed Feb. 8, 2002.

BACKGROUND OF THE INVENTION

The present invention relates to pyrimidine derivatives, compositions and medicaments containing the same, as well as processes for the preparation and use of such compounds, compositions and medicaments. Such pyrimidine derivatives are useful in the treatment of diseases associated with inappropriate angiogenesis.

The process of angiogenesis is the development of new blood vessels, generally capillaries, from pre-existing vasculature. Angiogenesis is defined as involving (i) activation of endothelial cells; (ii) increased vascular permeability; (iii) subsequent dissolution of the basement membrane and extravisation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and (vii) deposition of basement membrane and recruitment of perivascular cells to newly formed vessels. Normal angiogenesis is activated during tissue growth, from embryonic development through maturity, and then enters a period of relative quiescence during adulthood. Normal angiogenesis is also activated during wound healing, and at certain stages of the female reproductive cycle. Inappropriate angiogenesis has been associated with several disease states including various retinopathies; ischemic disease; atherosclerosis; chronic inflammatory disorders; and cancer. The role of angiogenesis in disease states is discussed, for instance, in Fan et al, Trends in Pharmacol Sci. 16:54-66; Shawver et al, DDT Vol. 2, No. 2 Feb. 1997; Folkmann, 1995, Nature Medicine 1:27-31.

In cancer, the growth of solid tumors has been shown to be angiogenesis dependent. (See Folkmann, J., J. Nat'l. Cancer Inst., 1990, 82, 4-6.) Consequently, the targeting of pro-angiogenic pathways in cancer treatment is a strategy being widely pursued in order to provide new therapeutics in these areas of great, unmet medical need. The role of tyrosine kinases involved in angiogenesis and in the vascularization of solid tumors has drawn interest. Until recently most interest in this area has focused on growth factors such as vascular endothelial growth factor (VEGF) and its receptors termed vascular endothelial growth factor receptor(s) (VEGFR). VEGF, a polypeptide, is mitogenic for endothelial cells in vitro and stimulates angiogenic responses in vivo. VEGF has also been linked to inappropriate angiogenesis (Pinedo, H. M. et al The Oncologist, Vol. 5, No. 90001, 1-2, April 2000). VEFGR(s) are protein tyrosine kinases (PTKs). PTKs catalyze the phosphorylation of specific tyrosyl residues in proteins involved in the regulation of cell growth and differentiation. (A. F. Wilks, Progress in Growth Factor Research, 1990, 2, 97-111; S. A. Courtneidge, Dev. Supp. I, 1993, 57-64; J. A. Cooper, Semin. Cell Biol., 1994, 5(6), 377-387; R. F. Paulson, Semin. Immunol., 1995, 7(4), 267-277; A. C. Chan, Curr. Opin. Immunol., 1996, 8(3), 394-401).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. et al J. Cell Biol. 1995:129:895-898). Of particular interest is VEGFR-2, which is a transmembrane receptor PTK expressed primarily in endothelial cells. Activation of VEGFR-2 by VEGF is a critical step in the signal transduction pathway that initiates tumor angiogenesis. VEGF expression may be constitutive to tumor cells and can also be upregulated in response to certain stimuli. One such stimuli is hypoxia, where VEGF expression is upregulated in both tumor and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3-10, April 2000).

Angiopoieten 1 (Ang1), a ligand for the endothelium-specific receptor tyrosine kinase TIE-2, is a novel angiogenic factor (Davis et al, Cell, 1996, 87:1161-1169; Partanen et al, Mol. Cell Biol, 12:1698-1707 (1992); U.S. Pat. Nos. 5,521,073; 5,879,672; 5,877,020; and 6,030,831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of an EGF-like domain and an immunoglobulin (IG) like domain, which consists of extracellular folding units, stabilized by intrachain disulfide bonds (Partanen et al Curr. Topics Microbiol. Immunol., 1999, 237:159-172). Unlike VEGF, which functions during the early stages of vascular development, Ang1 and its receptor TIE-2 function in the later stages of vascular development, i.e., during vascular remodeling (remodeling refers to formation of a vascular lumen) and maturation (Yancopoulos et al, Cell, 1998, 93:661-664; Peters, K. G., Circ. Res., 1998, 83(3):342-3; Suri et al, Cell 87, 1171-1180 (1996)).

Consequently, inhibition of TIE-2 would be expected to serve to disrupt remodeling and maturation of new vasculature initiated by angiogenesis thereby disrupting the angiogenic process. Furthermore, inhibition at the kinase domain binding site of VEGFR-2 would block phosphorylation of tyrosine residues and serve to disrupt initiation of angiogenesis. Presumably then, inhibition of TIE-2 and/or VEGFR-2 should prevent tumor angiogenesis and serve to retard or eradicate tumor growth. Accordingly, a treatment for cancer or other disorders associated with inappropriate angiogenesis could be provided.

The present inventors have discovered novel pyrimidine compounds, which are inhibitors of TIE-2 and/or VEGFR-2 kinase activity. Such pyrimidine derivatives are useful in the treatment of disorders, including cancer, associated with inappropriate angiogenesis.

BRIEF SUMMARY OF THE INVENTION

In one aspect of the present invention, there is provided a compound of Formula (I):

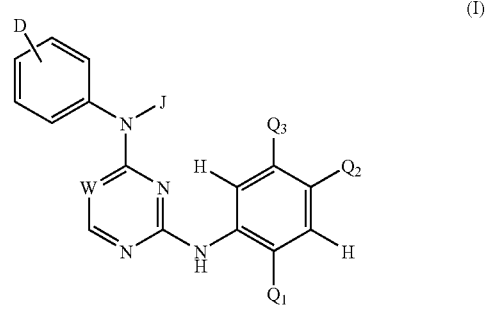

or a salt, solvate, or physiologically functional derivative thereof:

wherein:

W is N or C—R, wherein R is hydrogen, halogen, or cyano;

J is hydrogen, $C_1$-$C_4$ alkyl, $C_1$-$C_4$ haloalkyl, aralkyl, cyanoalkyl, —$(CH_2)_pC$=$CH(CH_2)_tH$, —$(CH_2)_pC$≡$C(CH_2)_tH$, or $C_3$-$C_7$ cycloalkyl;

p is 1, 2, or 3;

t is 0 or 1;

D is —N(H)(X);

X is the group defined by —$(X_1)$—$(X_2)_q$—$(X_3)$ wherein $X_1$ is C(O) or C(S) and q is 1, or $X_1$ is —C(O) or —S(O)$_2$ and q is 0, $X_2$ is N(H) or 0, and $X_3$ is alkyl, cycloalkyl, heterocyclyl, alkoxy, aryloxy, aralkoxy, aryl, aralkyl, or heteroaryl, or alkyl, cycloalkyl, heterocyclyl, alkoxy, aryloxy, aralkoxy, aryl, aralkyl, or heteroaryl substituted with at least one group defined by —$(X_4)_z$—$(X_5)$, $X_4$ is C(H)$_2$ where z is 0, 1, 2, 3, or 4, and $X_5$ is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, —CN, —NR'R', N(H)C(O)R", N(H)C(O)OR", N(H)C(O)NR'R', N(H)S(O)$_2$R", OR", OC(O)RR", C(O)R", SR", —S(O)R'", S(O)$_2$R'"R'", -or S(O)$_2$NR'R', where, R' is hydrogen, alkyl, cycloalkyl, heterocyclyl, —OR$^1$, —SR$^1$, —S(O)$_2$R$^1$, —S(O)R$^1$, or C(O)R$^1$;

R" is hydrogen, alkyl, cycloalkyl, heterocyclyl, —OR$^1$, —NR$^3$R$^4$, —S(O)$_2$R$^1$, —S(O)R$^1$, or C(O)R$^1$; and R'" is hydrogen, alkyl, cycloalkyl, heterocyclyl, —OR$^1$, or —NR$^3$R$^4$;

$Q_1$ is hydrogen, halogen, $C_1$-$C_2$ haloalkyl, $C_1$-$C_2$ alkyl, $C_1$-$C_2$ alkoxy, or $C_1$-$C_2$ haloalkoxy;

$Q_2$ is A$^1$ or A$^2$;

$Q_3$ is A$^1$ when $Q_2$ is A$^2$ and $Q_3$ is A$^2$ when $Q_2$ is A$^1$;

wherein

A$^1$ is hydrogen, halogen, $C_1$-$C_3$alkyl, $C_1$-$C_3$ haloalkyl, —OR$^1$, and A$^2$ is the group defined by -(Z)$_m$-(Z$^1$)-(Z$^2$), wherein Z is CH$_2$ and m is 0, 1, 2, or 3, or Z is NR$^2$ and m is 0 or 1, or Z is oxygen and m is 0 or 1, or Z is CH$_2$NR$^2$ and m is 0 or 1;

Z$^1$ is S(O)$_2$, S(O), or C(O); and

Z$^2$ is $C_1$-$C_4$ alkyl, cycloalkyl, heterocyclyl, NR$^3$R$^4$, aryl, arylamino, aralkyl, aralkoxy, or heteroaryl;

R$^1$ is hydrogen, alkyl, heterocyclyl, and —NR$^3$R$^4$;

R$^2$, R$^3$, and R$^4$ are each independently selected from hydrogen, hydroxy, alkoxy, aryloxy, aralkoxy, amino, alkylamino, arylamino, aralkylamino, $C_1$-$C_4$ alkyl, $C_3$-$C_7$ cycloalkyl, heterocyclyl, —S(O)$_2$R$^5$, and —C(O)R$^5$; and R$^5$ is $C_1$-$C_4$alkyl, or $C_3$-$C_7$ cycloalkyl.

In a second aspect of the present invention, there is provided a compound of Formula (II):

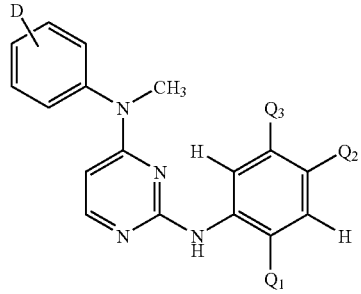

(II)

or a salt, solvate, or physiologically functional derivative thereof:

wherein:

D is —N(H)(X);

X is the group defined by —$(X_1)$—$(X_2)_q$—$(X_3)$ wherein $X_1$ is C(O) or C(S) and q is 1, or $X_1$ is —C(O) or —S(O)$_2$ and q is 0, $X_2$ is N(H) or 0, and $X_3$ is alkyl, cycloalkyl, heterocyclyl, alkoxy, aryloxy, aralkoxy, aryl, aralkyl, or heteroaryl, or alkyl, cycloalkyl, heterocyclyl, alkoxy, aryloxy, aralkoxy, aryl, aralkyl, or heteroaryl substituted with at least one group defined by —$(X_4)_z$—$(X_5)$, $X_4$ is C(H)$_2$ where z is 0, 1, 2, 3, or 4, and $X_5$ is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, —CN, —NR'R', N(H)C(O)R", N(H)C(O)OR", N(H)C(O)NR'R', N(H)S(O)$_2$R", OR", OC(O)R", C(O)R", SR", —S(O)R'", S(O)$_2$R'"R'",—or S(O)$_2$NR'R', where, R' is hydrogen, alkyl, cycloalkyl, heterocyclyl, —OR$^1$, —SR$^1$, —S(O)$_2$R$^1$, —S(O)R$^1$, or C(O)R$^1$;

R" is hydrogen, alkyl, cycloalkyl, heterocyclyl, —OR$^1$, —NR$^3$R$^4$, —S(O)$_2$R$^1$, —S(O)R$^1$, or C(O)R$^1$; and R'" is hydrogen, alkyl, cycloalkyl, heterocyclyl, —OR$^1$, or —NR$^3$R$^4$;

$Q_1$ is hydrogen, halogen, $C_1$-$C_2$ haloalkyl, $C_1$-$C_2$alkyl, $C_1$-$C_2$alkoxy, or $C_1$-$C_2$ haloalkoxy;

$Q_2$ is A$^1$ or A$^2$;

$Q_3$ is A$^1$ when $Q_2$ is A$^2$ and $Q_3$ is A$^2$ when $Q_2$ is A$^1$;

wherein

A$^1$ is hydrogen, halogen, $C_1$-$C_3$ alkyl, $C_1$-$C_3$ haloalkyl, —OR$^1$, and A$^2$ is the group defined by -(Z)$_m$-(Z$^1$)-(Z$^2$), wherein Z is CH$_2$ and m is 0, 1, 2, or 3, or Z is NR$^2$ and m is 0 or 1, or Z is oxygen and m is 0 or 1, or Z is CH$_2$NR$^2$ and m is 0 or 1;

Z$^1$ is S(O)$_2$, S(O), or C(O); and

Z$^2$ is $C_1$-$C_4$ alkyl, cycloalkyl, heterocyclyl, NR$^3$R$^4$, aryl, arylamino, aralkyl, aralkoxy, or heteroaryl;

R$^1$ is hydrogen, heterocyclyl, and —NR$^3$R$^4$;

R$^2$, R$^3$, and R$^4$ are each independently selected from hydrogen, hydroxy, alkoxy, aryloxy, aralkoxy, amino, alkylamino, arylamino, aralkylamino, $C_1$-$C_4$ alkyl, $C_3$-$C_7$ cycloalkyl, heterocyclyl, —S(O)$_2$R$^5$, and —C(O)R$^5$; and R$^5$ is $C_1$-$C_4$ alkyl, or $C_3$-$C_7$ cycloalkyl.

In a third aspect of the present invention, there is provided a compound of Formula (I):

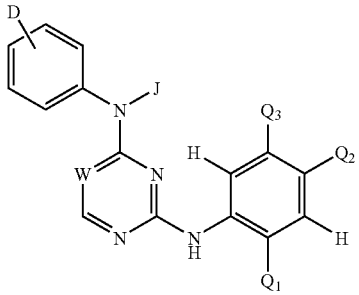

or a salt, solvate, or physiologically functional derivative thereof:

wherein:
W is N or C—R, wherein R is hydrogen, halogen, or cyano;
J is hydrogen, $C_1$-$C_4$ alkyl, $C_1$-$C_4$ haloalkyl, aralkyl, cyanoalkyl, —$(CH_2)_pC$=$CH(CH_2)_tH$, —$(CH_2)_pC$≡$C(CH_2)_tH$, or $C_3$-$C_7$ cycloalkyl;
p is 1, 2, or 3;
t is 0 or 1;
D is

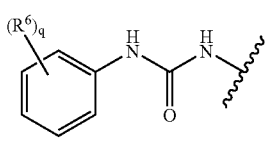

q is 1, 2, or 3;
$Q_1$ is hydrogen, halogen, $C_1$-$C_2$ haloalkyl, $C_1$-$C_2$ alkyl, $C_1$-$C_2$ alkoxy, or $C_1$-$C_2$ haloalkoxy;
$Q_2$ is $A^1$ or $A^2$;
$Q_3$ is $A^1$ when $Q_2$ is $A^2$ and $Q_3$ is $A^2$ when $Q_2$ is $A^1$;
wherein
  $A^1$ is hydrogen, halogen, $C_1$-$C_3$ alkyl, $C_1$-$C_3$ haloalkyl, —$OR^1$, and
  $A^2$ is the group defined by -$(Z)_m$-$(Z^1)$-$(Z^2)$, wherein
    Z is $CH_2$ and m is 0, 1, 2, or 3, or
    Z is $NR^2$ and m is 0 or 1, or
    Z is O and m is 0 or 1, or
    Z is $CH_2NR^2$ and m is 0 or 1;
    $Z^1$ is $S(O)_2$, S(O), or C(O); and
    $Z^2$ is $C_1$-$C_4$ alkyl, cycloalkyl, heterocyclyl, $NR^3R^4$, aryl, arylamino, aralkyl, aralkoxy, or heteroaryl;
$R^2$, $R^3$, and $R^4$ are each independently selected from hydrogen, hydroxy, alkoxy, aryloxy, aralkoxy, amino, alkylamino, arylamino, aralkylamino, $C_1$-$C_4$ alkyl, $C_3$-$C_7$ cycloalkyl, heterocyclyl, —$S(O)_2R^5$, and —$C(O)R^5$;
$R^5$ is $C_1$-$C_6$ alkyl, or $C_3$-$C_7$ cycloalkyl; and
$R^6$ is the group defined by —$(X_4)_z$—$(X_5)$, wherein
  $X_4$ is $C(H)_2$ where z is 0, 1, 2, 3, or 4, and
  $X_5$ is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, CN, —$NR^7R^7$, —$N(H)C(O)R^7$, —$N(H)C(O)OR^7$, —$N(H)C(O)NR^7R^7$, $N(H)S(O)_2R^7$, $N(H)S(O)_2NR^7R^7$, —$OC(O)R^7$, —$OC(O)NR^7R^7$, —$C(O)R^7$, —$C(O)NR^7R^7$, —$SR^7$, —$S(O)R^7$, $S(O)_2R^7R^7$, -or $S(O)_2NR^7R^7$; and $R^7$ is hydrogen, $C_1$-$C_6$ alkyl, $C_1$-$C_6$ haloalkyl, cycloalkyl, heterocyclyl, alkylamino, alkoxy, aryloxy, aralkoxy, arylamino, aralkylamino, aryl or heteroaryl.

In a fourth aspect of the present invention, there is provided a compound of formula (II):

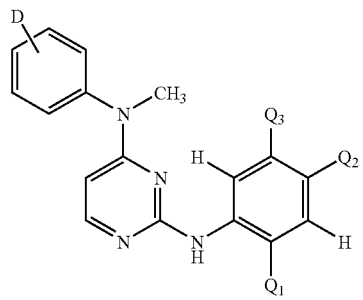

or a salt, solvate, or physiologically functional derivative thereof:

wherein:
D is

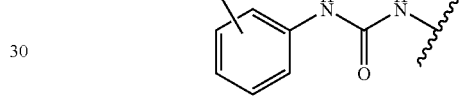

q is 1, 2, or 3;
$Q_1$ is hydrogen, halogen, $C_1$-$C_2$ haloalkyl, $C_1$-$C_2$ alkyl, $C_1$-$C_2$ alkoxy, or $C_1$-$C_2$ haloalkoxy;
$Q_2$ is $A^1$ or $A^2$;
$Q_3$ is A when $Q_2$ is $A^2$ and $Q_3$ is $A^2$ when $Q_2$ is $A^1$;
wherein
  $A^1$ is hydrogen, halogen, $C_1$-$C_3$ alkyl, $C_1$-$C_3$ haloalkyl, —$OR^1$, and
  $A^2$ is the group defined by -$(Z)_m$-$(Z^1)$-$(Z^2)$, wherein
    Z is $CH_2$ and m is 0, 1, 2, or 3, or
    Z is $NR^2$ and m is 0 or 1, or
    Z is O and m is 0 or 1, or
    Z is $CH_2NR^2$ and m is 0 or 1;
    $Z^1$ is $S(O)_2$, S(O), or C(O); and
    $Z^2$ is $C_1$-$C_4$ alkyl, cycloalkyl, heterocyclyl, $NR^3R^4$, aryl, arylamino, aralkyl, aralkoxy, or heteroaryl;
$R^2$, $R^3$, and $R^4$ are each independently selected from hydrogen, hydroxy, alkoxy, aryloxy, aralkoxy, amino, alkylamino, arylamino, aralkylamino, $C_1$-$C_4$ alkyl, $C_3$-$C_7$ cycloalkyl, heterocyclyl, —$S(O)_2R^5$, and —$C(O)R^5$;
$R^5$ is $C_1$-$C_6$ alkyl, or $C_3$-$C_7$ cycloalkyl; and
$R^6$ is the group defined by —$(X_4)_z$-$(X_5)$, wherein
  $X_4$ is $C(H)_2$ where z is 0, 1, 2, 3, or 4, and
  $X_5$ is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, CN, —$NR^7R^7$, —$N(H)C(O)R^7$, —$N(H)C(O)OR^7$, —$N(H)C(O)NR^7R^7$, $N(H)S(O)_2R^7$, $N(H)S(O)_2NR^7R^7$, —$OC(O)R^7$, $OC(O)NR^7R^7$, —$C(O)R^7$, —$C(O)NR^7R^7$, —$SR^7$, —$S(O)R^7$, $S(O)_2R^7R^7$, -or $S(O)_2NR^7R^7$; and
$R^7$ is hydrogen, $C_1$-$C_6$ alkyl, $C_1$-$C_6$ haloalkyl, cycloalkyl, heterocyclyl, alkylamino, alkoxy, aryloxy, aralkoxy, arylamino, aralkylamino, aryl or heteroaryl.

In a fifth aspect of the present invention, there is provided a compound of Formula (I):

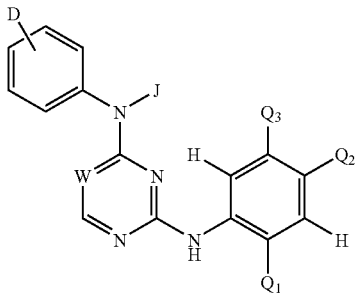

(I)

or a salt, solvate, or physiologically functional derivative thereof:

wherein:
W is N or C—R, wherein R is hydrogen, halogen, or cyano;
J is hydrogen, $C_1$-$C_4$alkyl, $C_1$-$C_4$ haloalkyl, aralkyl, cyanoalkyl, —$(CH_2)_pC$=$CH(CH_2)_tH$, —$(CH_2)_pC$=$C(CH_2)_tH$, or $C_3$-$C_7$ cycloalkyl;
p is 1, 2, or 3;
t is 0 or 1;
D is —$N(R^8)(X)$;
X is the group defined by —$(X_1)$—$(X_2)_q$—$(X_3)$ wherein
  $X_1$ is C(O) or C(S) and q is 1, or
  $X_1$ is —C(O) or —$S(O)_2$ and q is 0,
  $X_2$ is N(H) or 0, and
  $X_3$ is alkyl, cycloalkyl, heterocyclyl, alkoxy, aryloxy, aralkoxy, aryl, aralkyl, or heteroaryl, or
  alkyl, cycloalkyl, heterocyclyl, alkoxy, aryloxy, aralkoxy, aryl, aralkyl, or heteroaryl substituted with at least one group defined by —$(X_4)_z$—$(X_5)$,
  $X_4$ is $C(H)_2$ where z is 0, 1, 2, 3, or 4, and
  $X_5$ is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, —CN, —NR'R', N(H)C(O)R", N(H)C(O)OR", N(H)C(O)NR'R', N(H)S(O)$_2$R", OR", OC(O)R", C(O)R", SR", —S(O)R'", S(O)$_2$R'" R'", —or S(O)$_2$NR'R', where,
  R' is hydrogen, alkyl, cycloalkyl, heterocyclyl, —$OR^1$, —$SR^1$, —$S(O)_2R^1$, —$S(O)R^1$, or $C(O)R^1$;
  R" is hydrogen, alkyl, cycloalkyl, heterocyclyl, —$OR^1$, —$NR^3R^4$, —$S(O)_2R^1$, —$S(O)R^1$, or $C(O)R^1$; and
  R'" is hydrogen, alkyl, cycloalkyl, heterocyclyl, —$OR^1$, or —$NR^3R^4$;
$Q_1$ is hydrogen, halogen, $C_1$-$C_2$ haloalkyl, $C_1$-$C_2$ alkyl, $C_1$-$C_2$ alkoxy, or $C_1$-$C_2$ haloalkoxy;
$Q_2$ is $A^1$ or $A^2$;
$Q_3$ is $A^1$ when $Q_2$ is $A^2$ and $Q_3$ is $A^2$ when $Q_2$ is $A^1$; wherein
  $A^1$ is hydrogen, halogen, $C_1$-$C_3$alkyl, $C_1$-$C_3$ haloalkyl, —$OR^1$, and
  $A^2$ is the group defined by -$(Z)_m$-$(Z^1)$-$(Z^2)$, wherein
    Z is $CH_2$ and m is 0, 1, 2, or 3, or
    Z is $NR^2$ and m is 0 or 1, or
    Z is oxygen and m is 0 or 1, or
    Z is $CH_2NR^2$ and m is 0 or 1;
    $Z^1$ is $S(O)_2$, $S(O)$, or $C(O)$; and
    $Z^2$ is $C_1$-$C_4$ alkyl, cycloalkyl, heterocyclyl, $NR^3R^4$, aryl, arylamino, aralkyl, aralkoxy, or heteroaryl;
  $R^1$ is hydrogen, alkyl, heterocyclyl, and —$NR^3R^4$;

$R^2$, $R^3$, and $R^4$ are each independently selected from hydrogen, hydroxy, alkoxy, aryloxy, aralkoxy, amino, alkylamino, arylamino, aralkylamino, $C_1$-$C_4$ alkyl, $C_3$-$C_7$ cycloalkyl, heterocyclyl, —$S(O)_2R^5$, and —$C(O)R^5$;
$R^5$ is $C_1$-$C_4$alkyl, or $C_3$-$C_7$ cycloalkyl; and
$R^8$ is hydrogen or $C_1$-$C_3$ alkyl.

In a sixth aspect of the present invention, there is provided a pharmaceutical composition comprising a therapeutically effective amount of a compound of formula (I) or a salt, solvate, or a physiologically functional derivative thereof and one or more of pharmaceutically acceptable carriers, diluents and excipients.

In a seventh aspect of the present invention, there is provided a method of treating a disorder in a mammal, said disorder being mediated by at least one of inappropriate TIE-2 and VEGFR-2 activity, comprising: administering to said mammal a therapeutically effective amount of a compound of formula (I) or a salt, solvate or a physiologically functional derivative thereof.

In an eighth aspect of the present invention, there is provided a compound of formula (I), or a salt, solvate, or a physiologically functional derivative thereof for use in therapy.

In a ninth aspect of the present invention, there is provided the use of a compound of formula (I), or a salt, solvate, or a physiologically functional derivative thereof in the preparation of a medicament for use in the treatment of a disorder mediated by at least one of inappropriate TIE-2 and VEGFR-2 activity.

In a tenth aspect of the present invention, there is provided a method of treating a disorder in a mammal, said disorder being mediated by at least one of inappropriate TIE-2 and VEGFR-2 activity, comprising: administering to said mammal therapeutically effective amounts of (i) a compound of formula (I), or a salt, solvate or physiologically functional derivative thereof and (ii) an agent to inhibit growth factor receptor function.

In an eleventh aspect of the present invention, there is provided a method of treating a disorder in a mammal, said disorder being characterized by inappropriate angiogenesis, comprising: administering to said mammal a therapeutically effective amount of a compound of formula (I), or a salt, solvate or physiologically functional derivative thereof.

DETAILED DESCRIPTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight or branched chain hydrocarbon radical having from one to twelve carbon atoms, optionally substituted with substituents selected from the group consisting of $C_1$-$C_6$ alkyl, $C_1$-$C_6$ hydroxyalkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aryl, aryloxy, heteroaryl, aminosulfonyl optionally substituted by alkyl, nitro, cyano, halogen, or $C_1$-$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the terms "$C_1$-$C_2$ alkyl", "$C_1$-$C_3$ alkyl", "$C_1$-$C_4$ alkyl" and "$C_1$-$C_6$ alkyl" refer to an alkyl group, as defined above, containing at least 1, and at most 2, 3, 4, or 6, carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, and isopentyl.

As used herein, the term "halogen" refers to fluorine (F), chlorine (Cl), bromine (Br), or iodine (I) and the term "halo" refers to the halogen radicals fluoro (—F), chloro (—Cl), bromo (—Br), and iodo (—I).

As used herein, the terms "$C_1$-$C_2$ haloalkyl", "$C_1$-$C_3$ haloalkyl", "$C_1$-$C_4$ haloalkyl", and "($C_1$-$C_6$ haloalkyl" refer to an alkyl group as defined above containing at least 1, and at most 2, 3, 4, or 6, carbon atoms respectively substituted with at least one halo group, halo being as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo.

As used herein, the term "cycloalkyl" refers to a non-aromatic cyclic hydrocarbon ring. In a like manner the term "$C_3$-$C_7$ cycloalkyl" refers to a non-aromatic cyclic hydrocarbon ring having from three to seven carbon atoms and which optionally includes a $C_1$-$C_6$ alkyl linker through which it may be attached. The $C_1$-$C_6$ alkyl group is as defined above. Exemplary "$C_3$-$C_7$ cycloalkyl" groups useful in the present invention include, but are not limited to, cyclopropyl, cyclobutyl, cyclopentyl, cyclohexyl and cycloheptyl.

As used herein, the term "heterocyclic" or the term "heterocyclyl" refers to a three to twelve-membered non-aromatic heterocyclic ring, being saturated or having one or more degrees of unsaturation, containing one or more heteroatom substitutions selected from S, S(O), S(O)$_2$, O, or N, optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or $C_1$-$C_6$ perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, piperidine, piperazine, 2,4-piperazinedione, pyrrolidine, imidazolidine, pyrazolidine, morpholine, thiomorpholine, tetrahydrothiopyran, tetrahydrothiophene, and the like.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $c_1$-$C_6$ alkylsulfonylamino, arylsulfonoamino, alkylcarboxy, alkylcarboxyamide, oxo, hydroxy, mercapto, amino optionally substituted by alkyl or acyl, carboxy, tetrazolyl, carbamoyl optionally substituted by alkyl, aryl, or heteroaryl, aminosulfonyl optionally substituted by alkyl, acyl, aroyl, aroylamino, heteroaroyl, acyloxy, aroyloxy, heteroaroyloxy, alkoxycarbonyl, nitro, cyano, halogen, heteroaryl, heterocyclyl, aryl optionally substituted with aryl, halogen, $C_1$-$C_6$ alkyl, $C_1$-$C_6$ haloalkyl, or $C_1$-$C_6$ alkylsulfonyl, ureido, arylurea, alkylurea, cycloalkylurea, alkylthiourea, aryloxy, or aralkoxy, multiple degrees of substitution being allowed. Examples of "aryl" groups include, but are not limited to, phenyl, 2-naphthyl, 1-naphthyl, biphenyl, as well as substituted derivatives thereof.

As used herein, the term "aralkyl" refers to an aryl or heteroaryl group, as defined herein, attached through a $C_1$-$C_3$ alkylene linker, wherein the $C_1$-$C_3$ alkylene is as defined herein. Examples of "aralkyl" include, but are not limited to, benzyl, phenylpropyl, 2-pyridylmethyl, 3-isoxazolylmethyl, 5-methyl, 3-isoxazolylmethyl, and 2-imidazoyly ethyl.

As used herein, the term "heteroaryl" refers to a monocyclic five to seven membered aromatic ring, or to a fused bicyclic or tricyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl, or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "alkoxy" refers to the group $R_aO$—, where $R_a$ is alkyl as defined above and the term "$C_1$-$C_6$ alkoxy" refers to an alkoxy group as defined herein wherein the alkyl moiety contains at least 1, and at most 6, carbon atoms. Exemplary $C_1$-$C_6$ alkoxy groups useful in the present invention include, but are not limited to, methoxy, ethoxy, n-propoxy, isopropoxy, n-butoxy, and t-butoxy.

As used herein, the term "amino" refers to the group —$NH_2$.

As used herein the term "alkylamino" refers to the group —$NHR_a$ wherein $R_a$ is alkyl as defined above.

As used herein the term "arylamino" refers to the group —$NHR_a$ wherein $R_a$ is aryl as defined above.

As used herein the term "aralkylamino" refers to the group —$NHR_a$ wherein $R_a$ is an aralkyl group as defined above.

As used herein the term "aralkoxy" refers to the group $R_bR_aO$—, where $R_a$ is alkyl and Rb is aryl or heteroaryl all as defined above.

As used herein the term "aryloxy" refers to the group $R_aO$—, where $R_a$ is aryl or heteroaryl both as defined above.

As used herein the term "ureido" refers to the group —$NHC(O)NH_2$.

As used herein, the term "arylurea" refers to the group —$NHC(O)NHR_a$ wherein $R_a$ is aryl as defined above.

As used herein, the term "arylthiourea" refers to the group —$NHC(S)NHR_a$ wherein $R_a$ is aryl as defined above.

As used herein, the term "alkylurea" refers to the group —$NHC(O)NHR_a$ wherein $R_a$ is alkyl as defined above.

As used herein, the term "cycloalkylurea" refers to the group —$NHC(O)NHR_a$ wherein $R_a$ is cycloalkyl as defined above.

As used herein, the term "$C_3$-$C_7$ cycloalkoxy" refers to the group $R_aO$—, where $R_a$ is $C_3$-$C_7$ cycloalkyl as defined above. Exemplary $C_3$-$C_7$ cycloalkoxy groups useful in the present invention include, but are not limited to, cyclobutoxy, and cyclopentoxy.

As used herein, the term "haloalkoxy" refers to the group $R_aO$—, where $R_a$ is haloalkyl as defined above and the term "$C_1$-$C_6$ haloalkoxy" refers to a haloalkoxy group as defined herein wherein the haloalkyl moiety contains at least 1, and at most 6, carbon atoms. Exemplary $C_1$-$C_6$ haloalkoxy groups useful in the present invention include, but is not limited to, trifluoromethoxy.

As used herein, the term "alkylsulfanyl" refers to the group $R_aS$—, where $R_a$ is alkyl as defined above and the term "$C_1$-$C_6$ alkylsulfanyl" refers to an alkylsulfanyl group as defined herein wherein the alkyl moiety contains at least 1, and at most 6, carbon atoms.

As used herein, the term "haloalkylsulfanyl" refers to the group $R_aS$—, where $R_a$ is haloalkyl as defined above and the term "$C_1$-$C_6$ haloalkylsulfanyl" refers to a haloalkylsulfanyl group as defined herein wherein the alkyl moiety contains at least 1, and at most 6, carbon atoms.

As used herein, the term "alkylsulfenyl" refers to the group $R_aS(O)$—, where $R_a$ is alkyl as defined above and the term "$C_1$-$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group $R_aS(O)_2$—, where $R_a$ is alkyl as defined above and the term "$C_1$-$C_6$ alkylsulfonyl" refers to an alkylsulfonyl group as defined herein wherein the alkyl moiety contains at least 1, and at most 6, carbon atoms.

As used herein, the term "alkylsulfonylamino" refers to the group —$NHS(O)_2R_a$ wherein $R_a$ is alkyl as defined above and the term "$C_1$-$C_6$alkylsulfonylamino" refers to an alkylsulfonylamino group as defined herein wherein the alkyl moiety contains at least 1, and at most 6, carbon atoms.

As used herein, the term "arylsulfonylamino" refers to the group —$NHS(O)_2R_a$ wherein $R_a$ is aryl as defined above.

As used herein, the term "alkylcarboxyamide" refers to the group —$NHC(O)R_a$ wherein $R_a$ is alkyl, amino, or amino substituted with alkyl, aryl or heteroaryl as described above.

As used herein the term "alkylcarboxy" refers to the group —$C(O)R_a$ wherein $R_a$ is alkyl as described above.

As used herein, the term "oxo" refers to the group =O.

As used herein, the term "mercapto" refers to the group —SH.

As used herein, the term "carboxy" refers to the group —C(O)OH.

As used herein, the term "cyano" refers to the group —CN.

As used herein the term "cyanoalkyl" refers to the group —$CNR_a$, wherein $R_a$ is alkyl as defined above. Exemplary "cyanoalkyl" groups useful in the present invention include, but are not limited to, cyanomethyl, cyanoethyl, and cyanoisopropyl.

As used herein, the term "aminosulfonyl" refers to the group —$S(O)_2NH_2$.

As used herein, the term "carbamoyl" refers to the group —$C(O)NH_2$.

As used herein, the term "sulfanyl" shall refer to the group —S—.

As used herein, the term "sulfenyl" shall refer to the group —S(O)—.

As used herein, the term "sulfonyl" shall refer to the group —$S(O)_2$— or —$SO_2$—.

As used herein, the term "acyl" refers to the group $R_aC(O)$—, where $R_a$ is alkyl, cycloalkyl, or heterocyclyl as defined herein.

As used herein, the term "aroyl" refers to the group $R_aC(O)$—, where $R_a$ is aryl as defined herein.

As used herein, the term "aroylamino" refers to the group $R_aC(O)NH$—, where $R_a$ is aryl as defined herein.

As used herein, the term "heteroaroyl" refers to the group $R_aC(O)$—, where $R_a$ is heteroaryl as defined herein.

As used herein, the term "alkoxycarbonyl" refers to the group $R_aOC(O)$—, where $R_a$ is alkyl as defined herein.

As used herein, the term "acyloxy" refers to the group $R_aC(O)O$—, where $R_a$ is alkyl, cycloalkyl, or heterocyclyl as defined herein.

As used herein, the term "aroyloxy" refers to the group $R_aC(O)O$—, where $R_a$ is aryl as defined herein.

As used herein, the term "heteroaroyloxy" refers to the group $R_aC(O)O$—, where $R_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, $5^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or formula (II) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formulae (I) and (II) above as well as any wholly or partially equilibrated mixtures thereof. The present invention also covers the individual isomers of the compounds represented by the formulas above as mixtures with isomers thereof in which one or more chiral centers are inverted. Also, it is understood that any tautomers and mixtures of tautomers of the compounds of formulae (I) or (II) are included within the scope of the compounds of formulae (I) and (II).

It is to be understood that reference to compounds of formula (I) and formula (II) above, following herein, refers to compounds within the scope of both formula (I) and formula (II) as defined above with respect to W, D, X, $X_1$, $X_2$, $X_3$, $X_4$, Xs, $Q_1$, $Q_2$, $Q_3$, $A^1$, $A^2$, Z, $Z^1$, $Z^2$, $R^1$, $R^2$, $R^3$, $R^4$, $R^5$, $R^6$, $R^7$, R', R", R'" or unless specifically limited otherwise. It is also understood that the following embodiments, including uses and compositions, although recited with respect to formula (I) are also applicable to formula (II).

In one embodiment, the compound of formula (I) is a compound of formula (II):

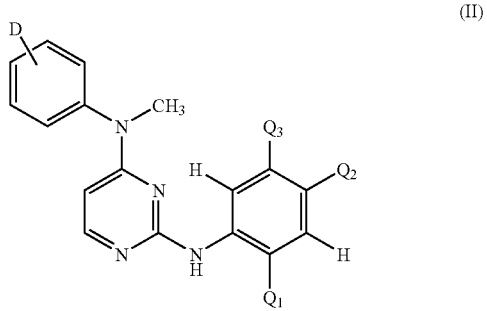

(II)

or salt, solvate, or physiologically functional derivative thereof, wherein D is N(H)X and X is as described above.

In another embodiment, the compound of formula (I) is a compound of formula (II):

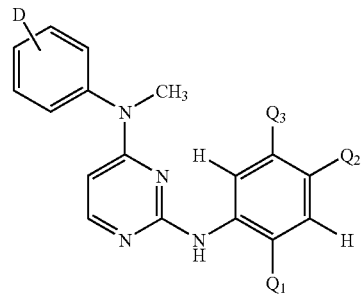

or salt, solvate, or physiologically functional derivative thereof, wherein D is

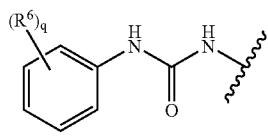

and $R^6$ is as described above.

It is understood that D is attached to the phenyl group of Formula (I) through a bond to the appropriate substituent indicated by

The appropriate attachments are further illustrated in the working examples recited below. Furthermore, it is understood that D may be attached meta, para, or ortho, preferably meta or para, more preferably para, to the indicated attachment to the rest of Formula (I).

In one embodiment, W is N. In a preferred embodiment, W is C—R wherein R is as described above. In a more preferred embodiment, W is C—R wherein R is hydrogen.

In one embodiment, J is hydrogen, $C_1$-$C_4$ alkyl, cyanoalkyl, or —$(CH_2)_pC\equiv C(CH_2)_tH$. In a preferred embodiment, J is hydrogen, methyl, ethyl, isopropyl, cyanomethyl, or —$(CH_2)_pC\equiv C(CH_2)_tH$, wherein p is 1 and t is 0. In a more preferred embodiment, J is methyl.

In one embodiment, D is —N(H)X, wherein X is the group defined by —$(X_1)$—$(X_2)_q$—$(X_3)$ and $X_1$ is C(O), $X_2$ is N(H), q is 1, and $X_3$ is alkyl, cycloalkyl, heterocyclyl, alkoxy, aryloxy, aralkoxy, aryl, aralkyl, or heteroaryl, or alkyl, cycloalkyl, heterocyclyl, alkoxy, aryloxy, aralkoxy, aryl, aralkyl, or heteroaryl substituted with at least one group defined by —$(X_4)_z$—(XS), where $X_4$ is —$(CH_2)_z$ where z is 0, 1, 2, 3, or 4, and Xs is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, CN, —NR'R', N(H)C(O)R", N(H)C(O)OR", N(H)C(O)NR'R', N(H)S(O)$_2$R", OR", OC(O)R", C(O)R", SR", —S(O)R'", S(O)$_2$R'" R'",—or S(O)$_2$NR'R'.

In a preferred embodiment, D is —N(H)X, wherein X is the group defined by —$(X_1)$—$(X_2)_q$—$(X_3)$ and $X_1$ is C(O), $X_2$ is N(H), q is 1, and $X_3$ is aryl or aryl substituted with at least one group defined by —$(X_4)_z$—$(X_5)$, where $X_4$ is —$(CH_2)_z$ where z is 0, 1, 2, 3, or 4, and $X_5$ is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, CN, —NR'R', N(H)C(O)R", N(H)C(O)OR", N(H)C(O)NR", N(H)S(O)$_2$R", OR", OC(O)R", C(O)R", SR", —S(O)R'", S(O)$_2$R'"R'",—or S(O)$_2$NR'R'.

In another preferred embodiment, D is —N(H)X, wherein X is the group defined by —$(X_1)$—$(X_2)_q$—$(X_3)$ and $X_1$ is C(O), $X_2$ is N(H), q is 1, and $X_3$ is phenyl or phenyl substituted with at least one group defined by —$(X_4)_z$—(XS), where $X_4$ is —$(CH_2)_z$ where z is 0 and $X_5$ is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, CN, —NR'R', N(H)C(O)R", N(H)C(O)OR", N(H)C(O)NR'R', N(H)S(O)$_2$R", OR", OC(O)R", C(O)R, SR", —S(O)R'", S(O)$_2$R'" R'",—or S(O)$_2$NR'R'.

As recited above, $X_3$ may be aryl, including phenyl, or aryl, including phenyl, substituted with at least one group defined by —$(X_4)_z$-$(X_5)$. It is understood that such aryl or phenyl group may also be optionally substituted as indicated above in the definition for "aryl" except where specifically limited.

In another embodiment, $Q_1$ is hydrogen, halogen, $C_1$-$C_2$ alkyl or $C_1$-$C_2$ alkoxy. In a preferred embodiment, $Q_1$ is hydrogen, chlorine, methyl, or methoxy.

In one embodiment, $Q_2$ is $A^1$ and $Q_3$ is $A^2$. In an alternative embodiment, $Q_2$ is $A^2$ and $Q_3$ is $A^1$.

In one embodiment, $Q_2$ is $A^2$ and $Q_3$ is $A^1$, wherein $A^1$ is hydrogen, halogen, or $C_1$-$C_3$ haloalkyl and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is S(O)$_2$, S(O), or C(O); and $Z^2$ is $C_1$-$C_4$alkyl or $NR^3R^4$ and wherein $R^2$, $R^3$, and $R^4$ are each independently selected from hydrogen, $C_1$-$C_4$alkyl, alkoxy, alkylamino, or amino. In a preferred embodiment, $Q_2$ is $A^2$ and $Q_3$ is $A^1$, wherein $A^1$ is hydrogen or chlorine and $A^2$ is the group defined by -$(Z)_m$-$(Z^1)$-$(Z^2)$, wherein Z is $CH_2$ and m is 0, 1, 2, or 3; $Z^1$ is S(O)$_2$; and $Z^2$ is $C_1$-$C_4$ alkyl or $NR^3R^4$, wherein $R^3$ and $R^4$ are each independently selected from hydrogen, $C_1$-$C_4$alkyl, alkoxy, alkylamino, or amino.

In one embodiment, $Q_2$ is $A^1$ and (13 is $A^2$, wherein $A^1$ is hydrogen, halogen, or $C_1$-$C_3$ alkyl and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$-$C_4$ alkyl or $NR^3R^4$, and wherein $R^2$, $R^3$, and $R^4$ are each independently selected from hydrogen, $C_1$-$C_4$alkyl, alkoxy, alkylamino, or amino. In a preferred embodiment, $Q_2$ is $A^1$ and $Q_3$ is $A^2$, wherein $A^1$ is hydrogen, methyl, or chlorine and $A^2$ is the group defined by -$(Z)_m$-$(Z^1)$-$(Z^2)$, wherein Z is $CH_2$ and m is 0, 1, 2, or 3; $Z^1$ is $S(O)_2$; and $Z^2$ is $C_1$-$C_4$alkyl or $NR^3R^4$, wherein $R^3$ and $R^4$ are each independently selected from hydrogen, $C_1$-$C_4$alkyl, alkoxy, alkylamino, or amino.

In a preferred embodiment, $X_1$ is C(O), $X_2$ is —N(H), $X_3$ is phenyl or phenyl substituted with at least one group defined by —$(X_4)_z$—$(X_5)$, where $X_4$ is —$(CH_2)_z$ where z is 0 and $X_5$ is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, CN, —NR'R', N(H)C(O)R", N(H)C(O)OR", N(H)C(O)NR'R', N(H)S(O)$_2$R", OR", OC(O)R", C(O)R", SR", —S(O)R'", S(O)$_2$R'" R'",—or S(O)$_2$NR'R', $Q_1$ is hydrogen, chlorine, methyl, or methoxy, $Q_2$ is $A^2$ and $Q_3$ is $A^1$, wherein $A^1$ is hydrogen or chlorine and $A^2$ is the group defined by -$(Z)_m$-$(Z^1)$-$(Z^2)$, wherein Z is $CH_2$ and m is 0, 1, 2, or 3; $Z^1$ is $S(O)_2$; and $Z^2$ is $C_1$-$C_4$ alkyl or $NR^3R^4$, wherein $R^3$ and $R^4$ are each independently selected from hydrogen, $C_1$-$C_4$alkyl, alkoxy, alkylamino, or amino.

In a preferred embodiment, $X_1$ is C(O), $X_2$ is —N(H), $X_3$ is phenyl or phenyl substituted with at least one group defined by —$(X_4)_z$—$(X_5)$, where $X_4$ is —$(CH_2)_z$ where z is 0 and $X_5$ is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, CN, —NR'R', N(H)C(O)R", N(H)C(O)OR", N(H)C(O)NR'R', N(H)S(O)$_2$R", OR", OC(O)R", C(O)R', SR", —S(O)R'", S(O)$_2$R'"R'",—or S(O)$_2$NR'R', $Q_1$ is hydrogen, chlorine, methyl, or methoxy, $Q_2$ is $A^1$ and $Q_3$ is $A^2$, wherein $A^1$ is hydrogen, methyl, or chlorine and $A^2$ is the group defined by -$(Z)_m$-$(Z^1)(Z^2)$, wherein Z is $CH_2$ and m is 0, 1, 2, or 3; $Z^1$ is $S(O)_2$; and $Z^2$ is $C_1$-$C_4$ alkyl or $NR^3R^4$, wherein $R^3$ and $R^4$ are each independently selected from hydrogen, $C_1$-$C_4$alkyl, alkoxy, alkylamino, or amino.

Specific examples of compounds of the present invention include the following:

3-{[4-(methyl{4-[({[4-(trifluoromethoxy)phenyl]amino}carbonyl)amino]phenyl}-amino) pyrimidin-2-yl]amino}benzenesulfonamide;

3-{[4-(methyl {4-[({[4-(trifluoromethyl)phenyl]amino}carbonyl)amino]phenyl}amino)pyrimidin-2-yl]amino}benzenesulfonamide;

3-[(4-{methyl[4-({[(4-phenoxyphenyl)amino]carbonyl}amino)phenyl]amino}-pyrimidin-2-yl)amino]benzenesulfonamide;

3-[(4-{methyl[4-({[(3-methylphenyl)amino]carbonyl}amino)phenyl]amino}pyrimidin-2-yl)amino]benzenesulfonamide;

3-({4-[[4-({[(2-chlorobenzyl)amino]carbonyl}amino)phenyl](methyl)amino]pyrimidin-2-yl}amino)benzenesulfonamide;

3-({4-[[4-({[(3-ethylphenyl)amino]carbonyl}amino)phenyl](methyl)amino]pyrimidin-2-yl}amino)benzenesulfonamide;

3-({4-[[4-({[(3-fluorophenyl)amino]carbonyl}amino)phenyl](methyl)amino]pyrimidin-2-yl}amino)benzenesulfonamide;

N-(3-chlorophenyl)-N'-{4-[(2-{5-(ethylsulfonyl)-2-methoxyphenyl]amino}pyrimidin-4-yl)(methyl)amino]phenyl}urea;

3-({4-[[4-({[(3-chlorophenyl)amino]carbonyl}amino)phenyl](methyl)amino]-pyrimidin-2-yl}amino)benzenesulfonamide;

3-({4-[[4-[(anilinocarbonyl)amino]phenyl}(methyl)amino]pyrimidin-2-yl}amino)benzenesulfonamide;

3-({4-[{4-[({[2-fluoro-5-(trifluoromethyl)phenyl]amino}carbonyl)amino]phenyl}-(methyl)amino]pyrimidin-2-yl}amino)benzenesulfonamide;

N-(3-fluorophenyl)-N'-(4-{methyl[2-({4-[(methylsulfonyl)methyl]phenyl}amino)pyrimidin-4-yl]amino}phenyl) urea hydrochloride;

N-[2-fluoro-5-(trifluoromethyl)phenyl]-N'-(4-{methyl[2-({4-(methylsulfonyl)methyl]phenyl}amino)pyrimidin-4-yl]amino}phenyl)urea hydrochloride;

3-({4-[{3-[({[2-fluoro-5-(trifluoromethyl)phenyl]amino}carbonyl)amino]phenyl}-(methyl)amino]pyrimidin-2-yl}amino)benzenesulfonamide;

3-({4-[[3-({[(3-chlorophenyl)amino]carbonyl}amino)phenyl](methyl)amino]-pyrimidin-2-yl}amino)benzenesulfonamide;

3-({4-[[3-({[(3-fluorophenyl)amino]carbonyl}amino)phenyl](methyl)amino]pyrimidin-2-yl}amino)benzenesulfonamide;

N-{4-[(2-{[5-(ethylsulfonyl)-2-methoxyphenyl]amino}pyrimidin-4-yl)(methyl)amino]phenyl}-N'-[2-fluoro-5-(trifluoromethyl)phenyl]urea;

N-{4-[(2-{[5-(ethylsulfonyl)-2-methoxyphenyl]amino}pyrimidin-4-yl)(methyl)amino]phenyl}-N'-(3-fluorophenyl)urea;

4-({4-[[4-({[(3-chlorophenyl)amino]carbonyl}amino)phenyl](methyl)amino]pyrimidin-2-yl}amino)benzenesulfonamide;

4-({4-[[4-({[(3-ethylphenyl)amino]carbonyl}amino)phenyl](methyl)amino]pyrimidin-2-yl}amino)benzenesulfonamide;

4-{[4-(methyl {4-[({[4-(trifluoromethoxy)phenyl]amino}carbonyl)amino]phenyl}amino)pyrimidin-2-yl]amino}benzenesulfonamide;

N-(4-{methyl [2-({3-[(methylsulfonyl)methyl]phenyl}amino)pyrimidin-4-yl]amino}phenyl)-N'-[4-(trifluoromethoxy)phenyl]urea;

N-(2,3-dihydro-1H-inden-5-yl)-N'-(4-{methyl[2-({3-[(methylsulfonyl)methyl]phenyl}amino)pyrimidin-4-yl]amino}phenyl)urea;

N-butyl-N'-(4-{methyl [2-({3-[(methylsulfonyl)methyl]phenyl}amino)pyrimidin-4-yl]amino}phenyl)urea;

4-({4-[[4-({[(3-fluorophenyl)amino]carbonyl}amino)phenyl](methyl)amino]pyrimidin-2-yl}amino)benzenesulfonamide;

4-({4-[[4-({[(3-chlorophenyl)amino]carbonyl}amino)phenyl](methyl)amino]pyrimidin-2-yl}amino)benzenesulfonamide;

4-({4-[{4-[({[2-fluoro-5-(trifluoromethyl)phenyl]amino}carbonyl)amino]phenyl) (methyl)amino]pyrimidin-2-yl}amino)benzenesulfonamide;

4-{[4-(methyl{4-[({[4-(trifluoromethyl)phenyl]amino}carbonyl)amino]phenyl}amino)pyrimidin-2-yl]amino}benzenesulfonamide;

N-[4-(benzyloxy)phenyl]-N'-(4-{methyl [2-({4-[(methylsulfonyl)methyl]phenyl}amino)pyrimidin-4-yl]amino}phenyl)urea;

N-(4-fluorophenyl)-N'-(4-{methyl[2-({4-[(methylsulfonyl)methyl]phenyl}amino) pyrimidin-4-yl]amino}phenyl) urea;

N-(4-{methyl[2-({3-[(methylsulfonyl)methyl]phenyl}amino)pyrimidin-4-yl]amino}phenyl)-N'-(2-phenylethyl)urea;

N-(4-{methyl[2-({3-[(methylsulfonyl)methyl]phenyl}amino)pyrimidin-4-yl]amino}phenyl)-N'-propylurea;

N-(2,6-dichlorophenyl)-N'-(4-{methyl[2-({3-[(methylsulfonyl)methyl]phenyl}mino)pyrimidin-4-yl]amino}phenyl) urea;

N-(4-acetyl phenyl)-N'-(4-{methyl[2-({3-[(methylsulfonyl)methyl]phenyl}mino)pyrimidin-4-yl]amino-3 phenyl) urea;

N-(4-{methyl [2-((3-[(methylsulfonyl)methyl]phenyl}amino)pyrimidin-4-yl]amino}phenyl)-N'-phenylurea;

N-[2-(dimethylamino)ethyl]-N'-(4-{methyl [2-({3-[(methylsulfonyl)ethyl]phenyl}amino)pyrimidin-4-yl]amino}phenyl)urea;

N-cyclohexyl-N-(4-{methyl [2-({3-[(methylsulfonyl)methyl]phenyl}amino)pyrimidin-4-yl]amino}phenyl)urea;

N-(4-{methyl[2-({3-[(methylsulfonyl)methyl]phenyl}amino)pyrimidin-4-yl]amino}phenyl)-N'-propylurea;

N-isopropyl-N'-(4-{methyl[2-({3-[(methylsulfonyl)methyl]phenyl}amino)pyrimidin-4-yl]amino}phenyl)urea;

N-(tert-butyl)-N-(4-{methyl[2-({3-[(methylsulfonyl)methyl]phenyl}amino)pyrimidin-4-yl]amino}phenyl)urea;

N-[3-({4-[[4-({[(3-chlorophenyl)amino]carbonyl}amino)phenyl](methyl)amino]yrimidin-2-yl}amino)benzyl]methanesulfonamide;

2-[4-({4-[(4-{[(ethylamino)carbonyl]amino}phenyl)(methyl)amino]pyrimidin-2-yl}amino)phenyl]-N-methylethanesulfonamide;

N-(4-{methyl[2-({4-[(methylsulfonyl)methyl]phenyl}amino)pyrimidin-4-yl]amino}phenyl)-N'-{4-[(4-methylpiperazin-1-yl)methyl]phenyl}urea;

N-(4-{methyl[2-({4-[(methylsulfonyl)methyl]phenyl}amino)pyrimidin-4-yl]amino}phenyl)-N'-{4-[(4-methylpiperazin-1-yl)carbonyl]phenyl}urea;

phenyl-4-{methyl[2-({3-[(methylsulfonyl)methyl]phenyl}amino)pyrimidin-4-yl]amino}phenylcarbamate;

benzyl-4-{methyl[2-({3-[(methylsulfonyl)methyl]phenyl}amino)pyrimidin-4-yl]amino}phenylcarbamate;

phenyl-4-[(2-{[3-(aminosulfonyl)-4-methylphenyl]amino}pyrimidin-4-yl)(methyl)amino]phenylcarbamate;

N-(4-{methyl[2-({3-[(methylsulfonyl)methyl]phenyl}amino)pyrimidin-4-yl]amino}phenyl)-1-phenylmethanesulfonamide;

N-(4-{methyl[2-({3-[(methylsulfonyl)methyl]phenyl}amino)pyrimidin-4-yl]amino}phenyl)-2-phenylacetamide;

N-(4-{methyl[2-({3-[(methylsulfonyl)methyl]phenyl}amino)pyrimidin-4-yl]amino}phenyl)-N'-phenylthiourea; and N-(4-{methyl[2-({3-[(methylsulfonyl)methyl]phenyl}amino)pyrimidin-4-yl]amino}phenyl)-N'-phenylguanidine;

or a salt, solvate, or physiologically functional derivative thereof.

Another example of a compound of formula (I) includes:
N-methyl-N-(4-{methyl[2-({3-[(methylsulfonyl)methyl]phenyl}amino)pyrimidin-4-yl]amino}phenyl)-N'-phenylurea; or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the Formulation, and the route of administration, and will ultimately be at the discretion of the attendant physician or veterinarian However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as combination with surgical therapy and radiotherapy. Combination therapies according to the present invention thus comprise the administration of at least one compound of formula (I) or a pharmaceutically acceptable salt or solvate thereof, or a physiologically functional derivative thereof, and the use of at least one other cancer treatment method. Preferably, combination therapies according to the present invention comprise the administration of at least one compound of formula (I) or a pharmaceutically acceptable salt or solvate thereof, or a physiologically functional derivative thereof, and at least one other pharmaceutically active agent, preferably an anti-neoplastic agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

The compounds of the Formula (I) or salts, solvates, or physiologically functional derivatives thereof and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I) or salts, solvates, or physiologically functional derivatives thereof with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts, solvates or physiologically functional derivatives thereof of formula I include the following:

(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methotrexate, cladrabine, cytarabine, mercaptopurine and thioguanine; and camptothecins such as 9-amino camptothecin, irinotecan, topotecan, CPT-11 and the various optical forms of 7-(4-methylpiperazino-methylene)-10, 11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumour antibiotics such as doxorubicin, daunomycin, epirubicin, idarubicin, mitomycin-C, dacttinomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; anti-androgens such as flutamide, nilutamide, bicalutamide, and cyproterone acetate; LHRH agonists and antagonists such as goserelin acetate and luprolide, testosterone 5α-dihydroreductase inhibitors such as finasteride; metalloproteinase inhibitors such as marimastat; anti-progestogens; urokinase plasminogen activator receptor function inhibitors; growth factor function inhibitors such as inhibitors of the functions of hepatocyte growth factor; erb-B2, erb-B4, epidermal growth factor receptor (EGFR), platelet derived growth factor receptor (PDGFR), vascular endothelial growth factor receptor (VEGFR, and TIE-2 (other than those VEGFR and TIE-2 inhibitors described in the present invention); and other tyrosine kinase inhibitors such as inhibitors of CDK2 and CDK4 inhibitors.

The compounds of formula (I) and salts, solvates and physiological functional derivatives thereof, are believed to have anticancer activity as a result of inhibition of the protein kinase TIE-2 and/or VEGFR-2 and its effect on selected cell lines whose growth is dependent on TIE-2 and/or VEGFR-2 protein kinase activity.

The present invention thus also provides compounds of formula (I) and pharmaceutically acceptable salts or solvates thereof, or physiologically functional derivatives thereof, for use in medical therapy, and particularly in the treatment of disorders mediated by at least one of inappropriate TIE-2 and VEGFR-2 activity.

The inappropriate TIE-2 and/or VEGFR-2 activity referred to herein is any TIE-2 and/or VEGFR-2 activity that deviates from the normal TIE-2 and/or VEGFR-2 activity expected in a particular mammalian subject. Inappropriate TIE-2 and/or VEGFR-2 activity may take the form of, for instance, an abnormal increase in activity, or an aberration in the timing and or control of TIE-2 and/or VEGFR-2 activity. Such inappropriate activity may result then, for example, from overexpression or mutation of the protein kinase leading to inappropriate or uncontrolled activation. Furthermore, it is also understood that unwanted TIE-2 and/or VEGFR-2 activity may reside in an abnormal source, such as a malignancy. That is, the level of TIE-2 and/or VEGFR-2 activity does not have to be abnormal to be considered inappropriate, rather the activity derives from an abnormal source. In a like manner, the inappropriate angiogenesis referred to herein is any angiogenic activity that deviates from the normal angiogenic activity expected in a particular mammalian subject. Inappropriate angiogenesis may take the form of, for instance, an abnormal increase in activity, or an aberration in the timing and or control of angiogenic activity. Such inappropriate activity may result then, for example, from overexpression or mutation of a protein kinase leading to inappropriate or uncontrolled activation. Furthermore, it is also understood that unwanted angiogenic activity may reside in an abnormal source, such as a malignancy. That is, the level of angiogenic activity does not have to be abnormal to be considered inappropriate, rather the activity derives from an abnormal source.

The present invention is directed to methods of regulating, modulating, or inhibiting TIE-2 and/or VEGFR-2 for the prevention and/or treatment of disorders related to unregulated TIE-2 and/or VEGFR-2 activity. In particular, the compounds of the present invention can also be used in the treatment of certain forms of cancer. Furthermore, the compounds of the present invention can be used to provide additive or synergistic effects with certain existing cancer chemotherapies, and/or be used to restore effectiveness of certain existing cancer chemotherapies and radiation.

The compounds of the present invention are also useful in the treatment of one or more diseases afflicting mammals which are characterized by cellular proliferation in the area of disorders associated with neo-vascularization and/or vascular permeability including blood vessel proliferative disorders including arthritis and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, organ transplant rejection and glomerulopathies; and metabolic disorders include psoriasis, diabetes mellitus, chronic wound healing, inflammation and neurodegenerative diseases.

A further aspect of the invention provides a method of treatment of a mammal suffering from a disorder mediated by at least one of inappropriate TIE-2 and VEGFR-2 activity, including susceptible malignancies, which includes administering to said subject an effective amount of a compound of formula (I) or a pharmaceutically acceptable salt, solvate, or a physiologically functional derivative thereof. In a preferred embodiment, the disorder is a susceptible cancer.

A further aspect of the invention provides a method of treatment of a mammal suffering from cancer which includes administering to said subject an effective amount of a compound of formula (I) or a pharmaceutically acceptable salt or solvate thereof, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by at least one of inappropriate TIE-2 and VEGFR-2 activity. In a preferred embodiment, the disorder is a susceptible cancer.

A further aspect of the present invention provides the use of a compound of formula (I), or a pharmaceutically acceptable salt or solvate thereof, or a physiologically functional derivative thereof, in the preparation of a medicament for the treatment of cancer and malignant tumors.

The mammal requiring treatment with a compound of the present invention is typically a human being.

In another embodiment, therapeutically effective amounts of the compounds of formula (I) or salts, solvates or physiologically derived derivatives thereof and agents which inhibit growth factor receptor function may be administered in combination to a mammal for treatment of a disorder mediated by at least one of inappropriate TIE-2 and VEGFR-2 activity, for instance in the treatment of cancer. Such growth factor receptors include, for example, EGFR, PDGFR, erbB2, erbB4, VEGFR, and/or TIE-2. Growth factor receptors and agents that inhibit growth factor receptor function are described, for instance, in Kath, John C., Exp. Opin. Ther. Patents (2000) 10(6):803-818 and in Shawver et al DDT Vol 2, No. 2 Feb. 1997.

The compounds of the formula (I) or salts, solvates, or physiologically functional derivatives thereof and the agent for inhibiting growth factor receptor function may be employed in combination concomitantly or sequentially in any therapeutically appropriate combination. The combination may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

In another aspect of the present invention, there is provided a method of treating a disorder in a mammal, said disorder being mediated by inappropriate angiogenesis, including: administering to said mammal a therapeutically effective amount of a compound of formula (I), or a salt, solvate or physiologically functional derivative thereof. In one embodiment, the inappropriate angiogenic activity is due to at least one of inappropriate VEGFR1, VEGFR2, VEGFR3, or TIE-2 activity. In another embodiment, the inappropriate angiogenesis is due to inappropriate VEGFR2 and TIE-2 activity. In a further embodiment, the method further includes administering a therapeutically effective amount of a VEGFR2 inhibitor along with the compounds of formula (I) or salts, solvates or physiologically functional derivatives thereof. Preferably the disorder is a susceptible cancer.

In another aspect of the present invention, there is provided the use of a compound of formula (I), or a salt, solvate or physiologically functional derivative thereof in the preparation of a medicament for use in treating a disorder in a mammal, said disorder being characterized by inappropriate angiogenesis. In one embodiment, the inappropriate angiogenic activity is due to at least one of inappropriate VEGFR1, VEGFR2, VEGFR3 or TIE-2 activity. In another embodiment, the inappropriate angiogenesis is due to inappropriate VEGFR2 and TIE-2 activity. In a further embodiment, the use further includes use of a VEGFR2 inhibitor to prepare said medicament.

The combination of a compound of formula (I) or salts, solvates, or physiologically functional derivatives thereof with a VEGFR2 inhibitor may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I). Those skilled in the art will recognize if a stereocenter exists in compounds of Formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L Eliel, S. H. Wilen, and L. N. Mander (Wiley-Interscience, 1994).

Compounds of Formula I and II can be prepared according to the synthetic sequences illustrated in Schemes-1, 2, 3, and 4 and further detailed in the Examples section following. In the embodiment where W is CH, typically 2,4-dichloropyrimidine undergoes a displacement reaction at C4 with an appropriate mono-protected dianiline to provide the 2-chloro-4-arylaminopyrimidine derivative (A). As shown in Scheme 1, for compounds of Formula I and II, wherein J is hydrogen, further displacement at C2 is carried out with an appropriate arylamine (C) to provide 2,4-diamino derivative (D). Deprotection of the amino protecting group (Ac or Boc group) under standard conditions (HCl or TFA) provides aniline (E), which is then converted to urea derivative ($X_1$ is C(O), $X_2$ is N(H)) (Formula I' and II'') using conventional methods (isocyanate or CDI/amine). In the embodiment where W is N, the dichlorotriazine is used instead of 2,4-dichloropyrimidine. In the embodiment where W is C—CN or C-halo, the appropriate 5-substituted 2,4-dichloropyrimidine is used instead of 2,4-dichloropyrimidine. The aniline (E) can be converted to a thiourea derivative of Formula I ($X_1$ is C(S), $X_2$ is N(H)) using isothiocyanate. The aniline (E) can also be converted to a carbamate derivative of Formula I ($X_1$ is C(O), $X_2$ is O) using chloroformate.

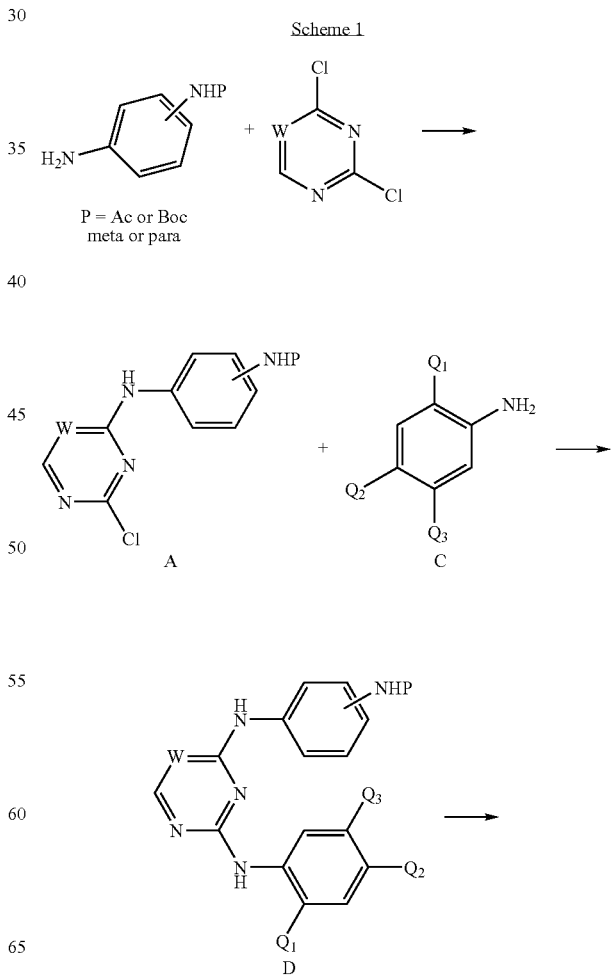

Scheme 1

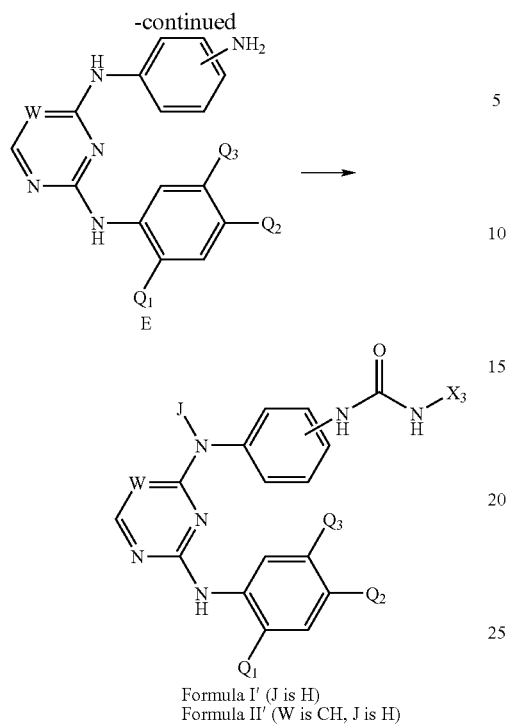

Formula I' (J is H)
Formula II' (W is CH, J is H)

As shown in Scheme 2, for compounds of Formula I and II, wherein $X_4$ is not hydrogen, subsequent N-alkylation of 2-chloro-4-arylamino derivative (A) under standard conditions affords the $N^4$-alkyl-2-chloro-4-arylamino derivative (B), which is treated with an arylamine (C) to provide 2,4-diamino derviative (D). Deprotection of the amino protecting group (Ac or Boc group) under standard conditions (HCl or TFA) provides aniline (E), which is then converted to urea derivative ($X_1$ is C(O), $X_2$ is N(H)) (Formula I' and II') using conventional methods (isocyanate or CDI/amine). The aniline (E) can be converted to thiourea derivative of Formula I ($X_1$ is C(S), $X_2$ is N(H)) using isothiocyanate. The aniline (E) can also be converted to carbamate derivative of Formula I ($X_1$ is C(O), $X_2$ is O) using chloroformate.

Scheme 2

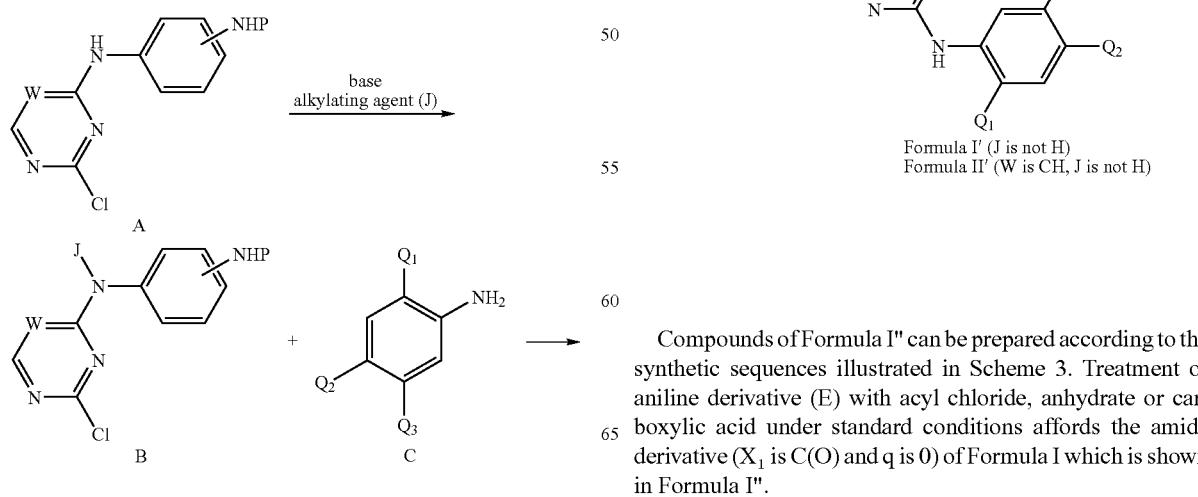

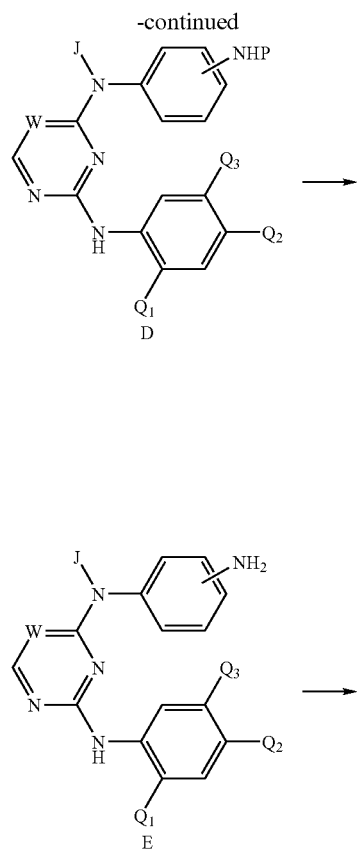

Formula I' (J is not H)
Formula II' (W is CH, J is not H)

Compounds of Formula I" can be prepared according to the synthetic sequences illustrated in Scheme 3. Treatment of aniline derivative (E) with acyl chloride, anhydrate or carboxylic acid under standard conditions affords the amide derivative ($X_1$ is C(O) and q is 0) of Formula I which is shown in Formula I".

Scheme 3

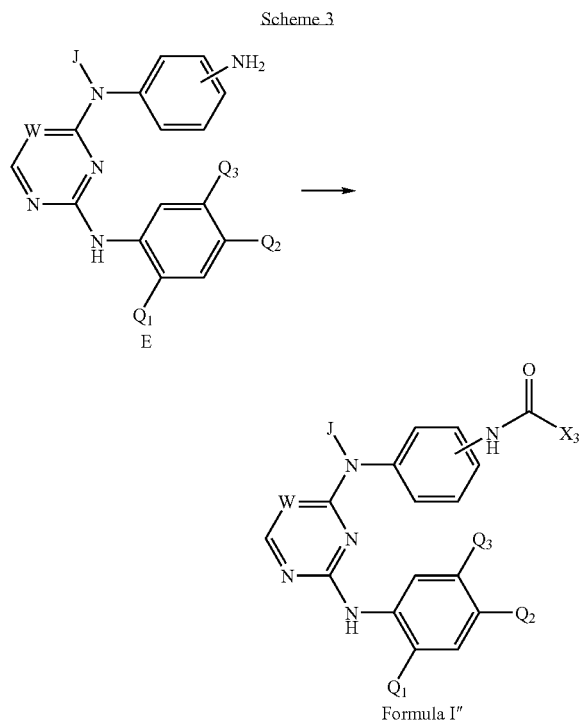

Formula I″

Compounds of Formula I‴ can be prepared according to the synthetic sequences illustrated in Scheme 4. Treatment of aniline derivative (E) with sulfonyl chloride under standard conditions affords the sulfonamide derivative ($X_1$ is $S(O)_2$ and q is 0) of Formula I which is shown in Formula I‴.

Scheme 4

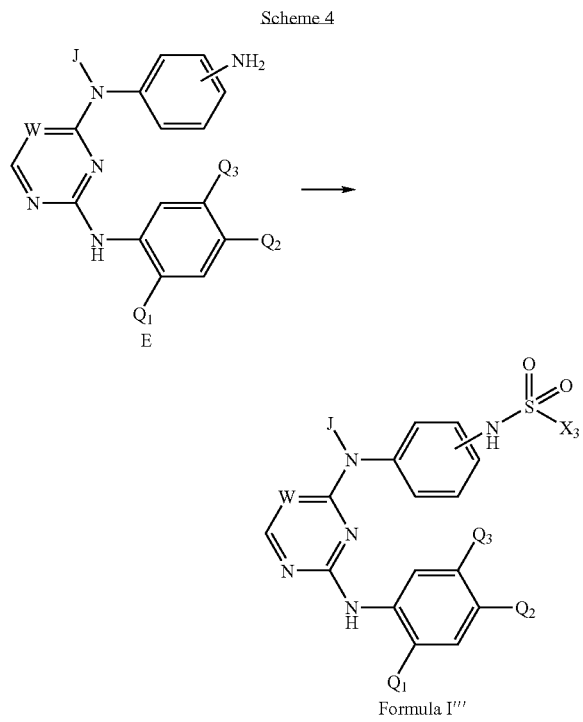

Formula I‴

The aniline moieties of Formula I and II depicted as structure C in Schemes 1, 2, 3 and 4 above, are available through multi-step organic synthesis familiar to one who is skilled in the art. The following schemes illustrate the methods that can be used to derive the anilines of structure C, which are incorporated into compounds of Formula I and II of the present invention.

As shown in Scheme 5, the appropriately substituted meta- or para-$NO_2$ benzylamine can be condensed with an alkyl- or arylsulfonyl chloride under suitable conditions (e.g., triethylamine, $CH_2Cl_2$) to provide a sulfonamide (F). The $NO_2$ moiety of F can be reduced using $SnCl_2$/conc. HCl or by hydrogenation (e.g., 10% Pd/C in methanol) to provide the desired aniline. Other embodiments of the present invention can be derived from anilines that are prepared as shown in Scheme 6. A nitro-substituted benzyl chloride (G) is converted to a sodium benzylsulfonate salt (H) by reaction at elevated temperature with $Na_2SO_3$ in a $H_2O$/dioxane mixture. Treatment of sodium benzylsulfonate salt (H) with $SOCl_2$ (cat. $DMF/CH_2Cl_2$) provides the corresponding sulfonyl-chloride (I), which can be treated with an amine to provide a sulfonamide (J). Reduction of the nitro group in sulfonamide (J) can be accomplished in similar fashion as described above in Scheme 5.

Scheme 5

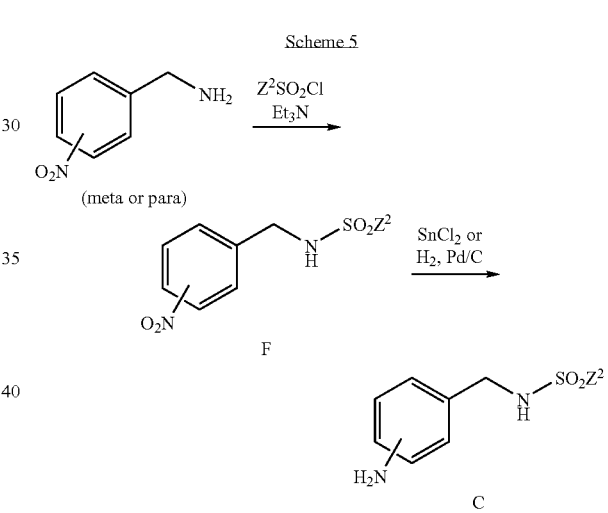

Scheme 6

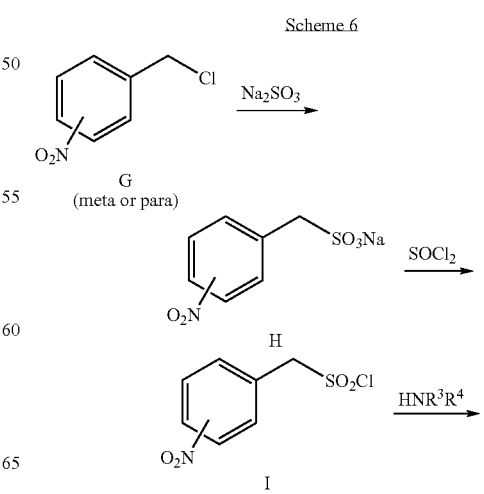

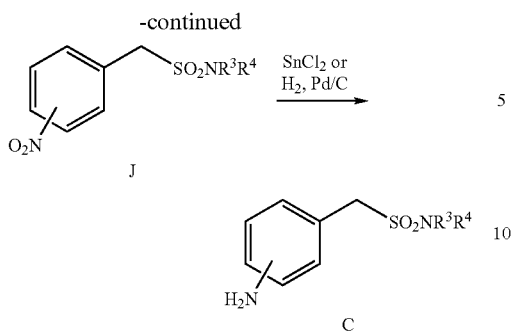

Scheme 7 depicts the synthesis of other anilines of structure C that are useful in the preparation of compounds of Formula I and II. An appropriate thiolate anion undergoes a displacement reaction with a nitro-substituted benzyl chloride (G) to provide a benzylic sulfide (K). Oxidation of the sulfide, for example with mCPBA, provides the corresponding sulfone, which is then reduced by standard methods to the desired aniline (C).

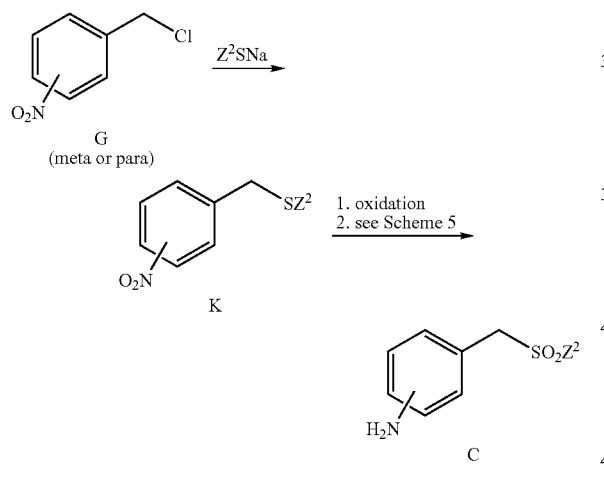

Scheme 8 depicts the synthesis of other anilines of structure C that are useful in the preparation of compounds of Formula I and II. The 2-methoxyacetanilide undergoes chlorosulfonylation under standard conditions to provide the expected arylsulfonyl chloride (L). Amination of L with an amine affords a sulfonamide, which is hydrolyzed under appropriate conditions to provide the desired aniline (C).

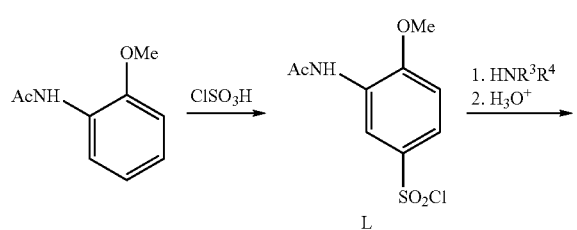

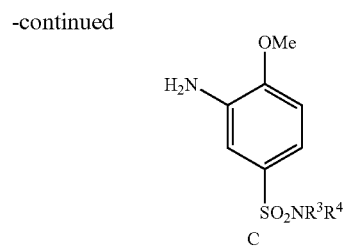

Scheme 9 depicts the synthesis of other anilines of structure C that are useful in the preparation of compounds of Formula I and II. The para-methoxy sulfenimide (M) can be prepared as described in the prior art. Mitsunobu-type substitution with an alcohol provides the phenyl sulfide (N). (In certain cases, one who is skilled in the art will recognize that the same phenylsulfide (N) can be derived by alkylation of the para-methoxy thiophenoxide anion with an alkyl halide.) Oxidation of sulfide (N) affords a sulfone (O), which undergoes nitration to provide the methoxynitrosulfone (P). Methoxynitrosulfone (P) is reduced as already described by the earlier scheme to the aniline (C).

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams);
L (liters);
μL (microliters);
M (molar);
i.v. (intravenous);
MHz (megahertz);
mmol (millimoles);
min (minutes); h (hours);
mp (melting point);
$T_r$ (retention time);
MeOH (methanol);
TEA (triethylamine);
TFAA (trifluoroacetic anhydride);
DMSO (dimethylsulfoxide);
DME (1,2-dimethoxyethane);
DCE (dichloroethane);
DMPU (N,N'-dimethylpropyleneurea);
IBCF (isobutyl chloroformate);
HOSu (N-hydroxysuccinimide);
mCPBA (meta-chloroperbenzoic acid;
BOC (tert-butyloxycarbonyl);
DCC (dicyclohexylcarbodii mide);
Ac (acetyl); atm (atmosphere);
TMSE (2-(trimethylsilyl)ethyl);
TIPS (triisopropylsilyl);
DMAP (4-dimethylaminopyridine);
ATP (adenosine triphosphate);
DMEM (Dulbecco's modified Eagle medium);
HPLC (high pressure liquid chromatography);
BOP (bis(2-oxo-3-oxazolidinyl)phosphinic chloride);
mg (milligrams);
mL (milliliters);
psi (pounds per square inch);
mM (millimolar);
Hz (Hertz);
mol (moles);
rt (room temperature);
h (hours);
TLC (thin layer chromatography);
RP (reverse phase);
i-PrOH (isopropanol);
TFA (trifluoroacetic acid);
THF (tetrahydrofuran);
AcOEt (ethyl acetate);
DCM (dichloromethane);
DMF (N,N-dimethylformramide);
(CDI (1,1-carbonyldiimidazole);
HOAc (acetic acid);
HOBT (1-hydroxybenzotriazole);
EDC (ethylcarbodiimide hydrochloride);
FMOC (9-fl uorenyl methoxycarbonyl);
CBZ (benzyloxycarbonyl);
atm (atmosphere);
TMS (trimethylsilyl);
TBS (t-butyldimethylsilyl);
BSA (bovine serum albumin);
HRP (horseradish peroxidase);
TBAF (tetra-n-butylammonium fluoride);
HBTU (O-Benzotriazole-1-yl-N,N,N',N'-tetramethyluronium hexafluorophosphate).
HEPES (4-(2-hydroxyethyl)-1-piperazine ethane sulfonic acid);
DPPA (diphenylphosphoryl azide);
fHNO₃ (fumed HNO₃); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Varian VXR-300, a Varian Unity-300, a Varian Unity-400 instrument, a Brucker AVANCE-400, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

HPLC were recorded on a Gilson HPLC or Shimazu HPLC system by the following conditions. Column: 50×4.6 mm (id) stainless steel packed with 5 μm Phenomenex Luna C-18; Flow rate: 2.0 mL/min; Mobile phase: A phase=50 mM ammonium acetate (pH 7.4), B phase=acetonitrile, 0-0.5 min (A: 100%, B: 0%), 0.5-3.0 min (A: 100-0%, B: 0-100%), 3.0-3.5 min (A: 0%, B: 100%), 3.5-3.7 min (A: 0-1000%0, B: 100-0%), 3.7-4.5 min (A: 100%, B: 0%); Detection: UV 254 nm; Injection volume: 3 μL.

Low-resolution mass spectra (MS) were recorded on a JOEL JMS-AX505HA, JOEL SX-102, or a SCIEX-APliii spectrometer; LC-MS were recorded on a micromass 2MD and Waters 2690; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck).

Intermediate Example 1

N-{4-[(2-chloropyrimidin-4-yl)amino]phenyl}acetamide

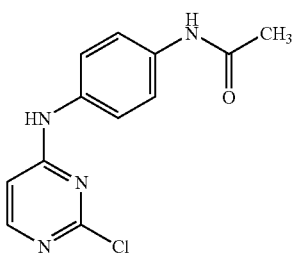

To a stirred solution of N-(4-aminophenyl)acetamide (5 g, 0.033 mol) and NaHCO₃ (5.6 g, 0.067 mol) in THF (20 mL) and ethanol (80 mL) was added 2,4-dichloropyrimidine (5.95 g, 0.04 mol) at room temperature. The reaction was gradually heated to 85° C. After the reaction was stirred for four hours at 85° C. under N₂, the suspension was filtered and washed thoroughly with ethanol. The filtrate was concentrated under reduced pressure, and the resulting solid was washed with EtOAc to remove excess 2,4-dichloropyrimidine to yield 8.35 g (95.5% yield) of N-{4-[(2-chloropyrimidin-4-yl)amino]phenyl}acetamide as an off-white solid.

Intermediate Example 2

N-{4-[(2-chloropyrimidin-4-yl)(methyl)amino]phenyl}acetamide

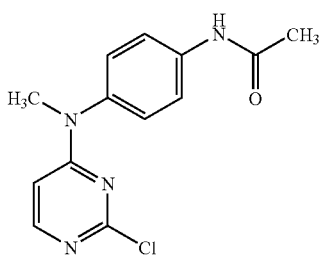

To a stirred solution of the Intermediate 1 (1.5 g, 5.71 mmol) in DMF (11 ml) was added CS₂CO₃ (2.37 g, 0.017 mol) and MeI (0.39 ml, 6.28 mmol) at room temperature. Mixture was stirred at rt for overnight. The reaction mixture was poured into ice-water bath (~150 ml), and the precipitate was collected via filtration and washed with water. The precipitate was air-dried to afford N-{4-[(2-chloropyrimidin-4-yl)(methyl)amino]phenyl}acetamide as a yellow solid (1.32 g, 84%).

Intermediate Example 3

N-{4-[(2-{[3-(aminosulfonyl)phenyl]amino}pyrimidin-4-yl)(methyl)amino]phenyl}acetamide

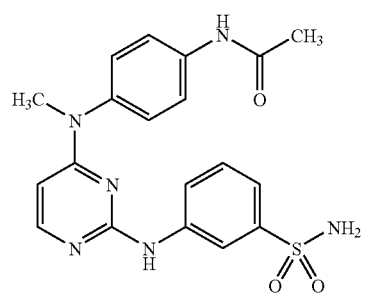

To a solution of Intermediate Example 2 (200 mg, 0.723 mmol) and 3-aminobenzenesulfonamide (124.5 mg, 0.723 mmol) in isopropanol (6 ml) was added 4 drops of conc. HCl. The mixture was heated at 85° C. overnight in sealed tube. The mixture was evaporated to dryness, and the crude product was progressed to next step without further purification.

Intermediate Example 4

3-({4-[(4-aminophenyl)(methyl)amino]pyrimidin-2-yl}amino)benzene-sulfonamide

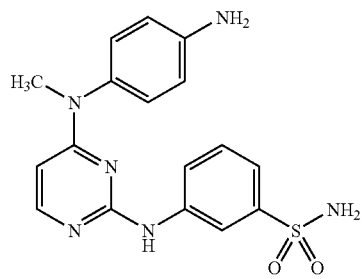

To the crude product of Intermediate Example 3 was added 3 ml of conc. HCl. The mixture was heated at 90° C. for 4 h under N₂. The mixture was cooled to rt and diluted with EtOAC. The mixture was basified with NaHCO₃ slowly. The solution was extracted thoroughly with EtOAc (×3). The combined organic layers were dried over anhydrous MgSO₄, filtered and evaporated. The precipitate was collected, and 3-({4-[(4-aminophenyl)(methyl)amino]pyrimidin-2-yl}amino)benzenesulfonamide was isolated as an off-white solid (180 mg, 67% from Intermediate Example 2).

Unless otherwise indicated, the compounds of Intermediate Examples 5-12 were prepared according to the general procedures set forth above in Intermediate Example 3-4, using the suitably substituted anilines.

Intermediate Example 5

4-({4-[(4-aminophenyl)(methyl)amino]pyrimidin-2-yl}amino)benzenesulfonamide

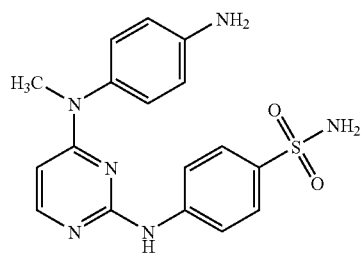

Intermediate Example 6

N⁴-(4-aminophenyl)-N⁴-methyl-N²-{3-[(methylsulfonyl)methyl]phenyl}pyrimidine-2,4-diamine

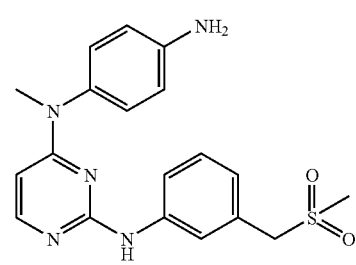

Intermediate Example 7

N$^4$-(4-aminophenyl)-N$^4$-methyl-N$^2$-{4-[(methylsulfonyl)methyl]phenyl}pyrimidine-2,4-diamine

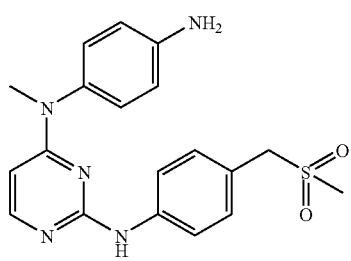

Intermediate Example 8

N-[3-({4-[(4-aminophenyl)(methyl)amino]pyrimidin-2-yl}amino)benzyl]methanesulfonamide

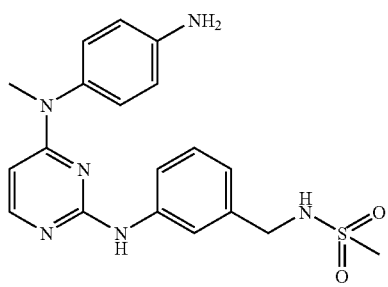

Intermediate Example 9

N-[3-({4-[(4-aminophenyl)(methyl)amino]pyrimidin-2-yl}amino)benzyl]methanesulfonamide

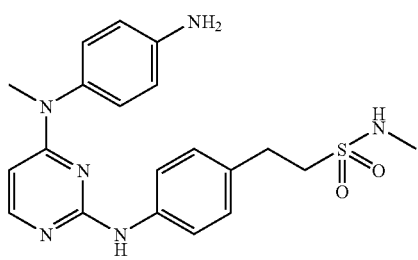

Intermediate Example 10

N-{4-[(2-chloropyrimidin-4-yl)(methyl)amino]phenyl}-N-methylacetamide

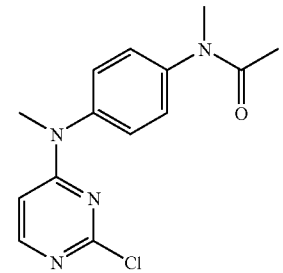

To a solution of Intermediate Example 1 (1.5 g, 5.7 mmol) and cesium carbonate (5.6 g, 17 mmol) in DMF (10 ml) was added methyl iodide (0.53 mL, 8.6 mmol) and the mixture was stirred at rt for 64 hours. The reaction mixture was diluted with water and cooled. The resulting solid was filtered off and dried on a vacuum pump. The solids were purified with silica gel to give the title compound as an off-white solid (0.79 g, 47%). $^1$H NMR (300 MHz, d$_6$-DMSO) δ 8.02 (d, $_1$H), 7.45 (m, 4H), 6.36 (d, $_1$H), 3.40 (s, 3H), 3.19 (s, 3H), 1.85 (s, 3H). MS (ES+, m/z) 291 [M+H].

Intermediate Example 11

N-methyl-N-(4-{methyl[2-({3-[(methylsulfonyl)methyl]phenyl}amino) pyrimidin-4-yl]amino}phenyl)acetamide

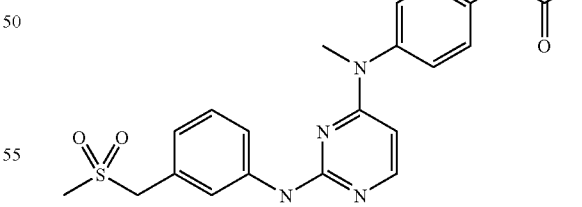

Compound was prepared using protocol similarly described in Intermediate Example 3 except Intermediate Example 10 is used instead of Intermediate Example 2, and 3-[(methylsulfonyl)methyl]aniline is used instead of 3-aminobenzenesulfonamide. $^1$H NMR (400 MHz, DMSO-d$_6$) δ 9.31 (s, 1H), 7.93 (d, 1H), 7.82 (s, 1H), 7.74 (s, 1H), 7.43 (s, 3H), 7.23 (t, 1H), 6.95 (d, 1H), 6.54 (m, 1H), 5.88 (d, 1H), 4.39 (s, 2H), 3.45 (s, 3H), 3.20 (s, 3H), 2.92 (s, 3H), 1.84 (s, 3H). MS (ES+, m/z) 462 (M+Na).

Intermediate Example 12

N[4]-methyl-N[4]-[4-(methylamino)phenyl]-N[2]-{3-[(methylsulfonyl)methyl]phenyl}pyrimidine-2,4-diamine

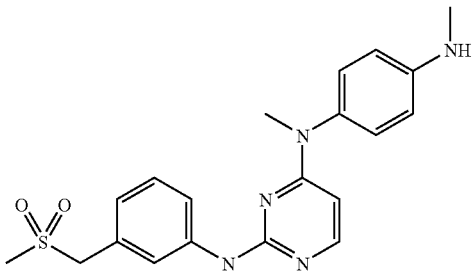

Compound was prepared using protocol similarly described in Intermediate Example 4 except Intermediate Example 11 is used instead of Intermediate Example 3. $^1$H NMR (400 MHz, DMSO-$d_6$) δ 9.20 (s, 1H), 7.88 (s, 1H), 7.79 (d, 1H), 7.69 (d, 1H), 7.23 (t, 1H), 7.01 (d, 2H), 6.92 (d, 1H), 6.60 (d, 2H), 5.84 (d, 1H), 5.67 (d, 1H), 4.37 (s, 2H), 3.35 (s, 3H), 2.91 (s, 3H), 2.70 (d, 3H). MS (APCl, m/z) 398 (M+H).

Example 1

3-{[4-(methyl{4-[({[4-(trifluoromethoxy)phenyl]amino}carbonyl)amino]phenyl}-amino)pyrimidin-2-yl]amino}benzenesulfonamide

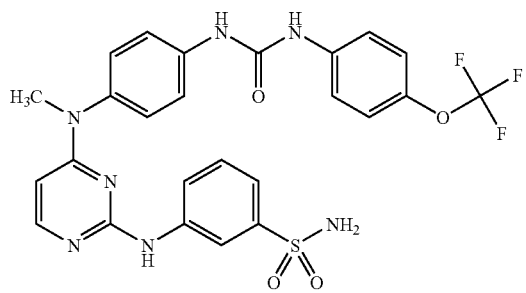

To a solution of Intermediate Example 4 (40 mg) in acetone (1 ml) was added (4-trifluoromethoxy)phenyl isocyanate (1 eqv.). The mixture was capped and stirred at 40° C. overnight. The mixture was evaporated to dryness and then triturated with Et$_2$O. The solid was collected via filtration. 3-{[4-(methyl{4-[({[4-(trifluoromethoxy)phenyl]amino}-carbonyl)amino]phenyl})amino) pyrimidin-2-yl]amino}benzenesulfonamide was isolated at an off-white solid. $^1$H NMR (300 MHz, DMSO-$d_6$) δ 9.52 (br s, 1H), 8.92 (br s, 1H), 8.87 (br s, 1H), 8.55 (br s, 1H), 7.87 (d, J=6.0 Hz, 1H), 7.79 (d, J=7.9, 1H), 7.57 (m, 4H), 7.33 (m, 8H), 5.78 (d, J=6.0 Hz, 1H), 3.43 (s, 3H). MS (ES+, m/z) 574 (M+H).

Unless otherwise indicated, the compounds of Examples 2-36 were prepared according to the general procedures set forth above in Example 1.

Example 2

3-{[4-(methyl{4-[({[4-(trifluoromethyl)phenyl]amino}carbonyl)amino]phenyl}amino) pyrimidin-2-yl]amino}benzenesulfonamide

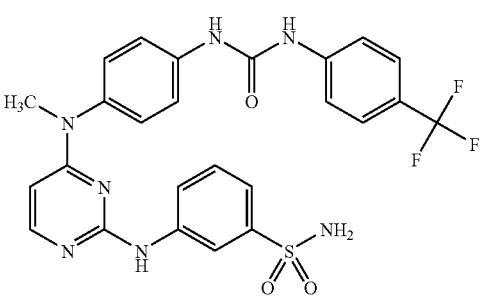

$^1$H NMR (300 MHz, DMSO-$d_6$) δ 9.52 (br s, 1H), 9.14 (br s, 1H), 8.96 (br s, 1H), 8.55 (br s, 1H), 7.84 (m, 2H), 7.63 (m, 6H), 7.33 (m, 6H), 5.78 (d, J=6.0 Hz, 1H), 3.43 (s, 3H). MS (ES+, m/z) 558 (M+H).

Example 3

3-[(4-{methyl[4-({[(4-phenoxyphenyl)amino]carbonyl}amino)phenyl]amino}-pyrimidin-2-yl)amino]benzenesulfonamide

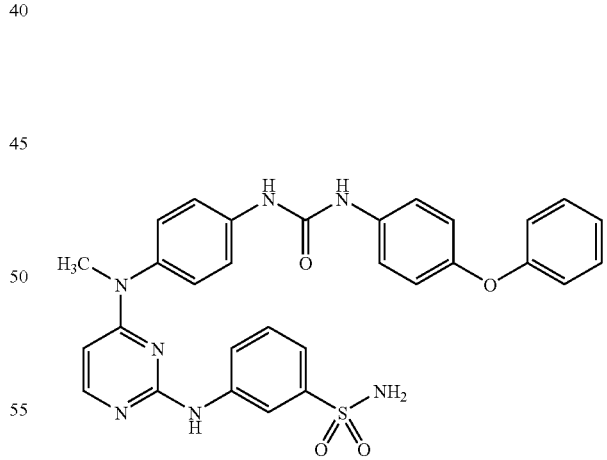

$^1$H NMR (300 MHz, DMSO-$d_6$) δ 9.51 (br s, 1H), 8.80 (br s, 1H), 8.65 (br s, 1H), 8.56 (br a, 1H), 8.72 (br s, 1H), 7.87 (d, J=6.0 Hz, 1H), 7.79 (d. J=7.8 Hz, 1H), 7.40 (m, 13H), 7.09 (t, J=7.3 Hz, 1H), 6.97 (m, 2H), 5.78 (d, J=6 Hz, 1H), 3.43 (brs, 3H). MS (ES+, m/z) 582 (M+H).

Example 4

3-[(4-{methyl[4-({[(3-methylphenyl)amino]carbonyl}amino)phenyl]amino}pyrimidin-2-yl)amino]benzenesulfonamide

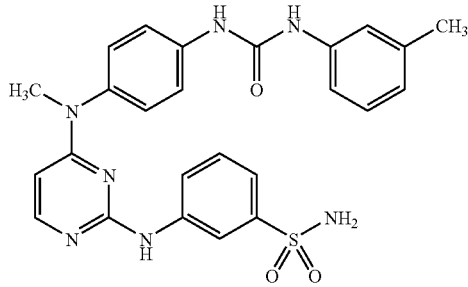

¹H NMR (300 MHz, DMSO-d₆) δ 9.51 (br s, 1H), 8.79 (br s, 1H), 8.62 (br s, 1H), 8.55 (br s, 1H), 7.87 (d, J=6 Hz, 1H), 7.79 (d, J=7.7 Hz, 1H), 7.28 (m, 9H), 6.80 (d, J=7.3 Hz, 1H), 5.77 (d, J=6.0 Hz, 1H), 3.43 (s, 3H), 2.28 (s, 3H). MS (ES+, m/z) 504 (M+H).

Example 5

3-({4-[[4-({[(2-chlorobenzyl)amino]carbonyl}amino)phenyl](methyl)amino]pyrimidin-2-yl}amino)benzenesulfonamide

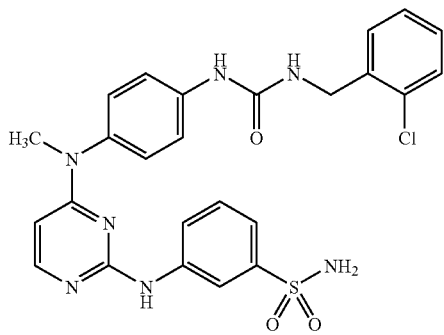

¹H NMR (400 MHz, DMSO-d₆) δ 9.49 (br s, 1H), 8.83 (br s, 1H), 8.54 (br s, 1H), 7.80 (m, 2H), 7.33 (m, 12H), 6.69 (br s, 1H), 5.73 (d, J=5.7 Hz, 1H), 4.37 (d, J=5.2 Hz, 2H), 3.39 (s, 3H). MS (ES+, m/z) 538 (M+H).

Example 6

3-({4-[[4-({[(3-ethylphenyl)amino]carbonyl}amino)phenyl](methyl)amino]pyrimidin-2-yl}amino)benzenesulfonamide

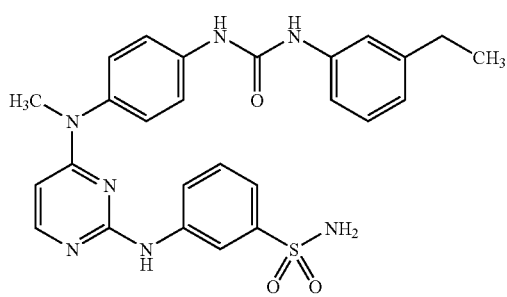

¹H NMR (400 MHz, DMSO-d₆) δ 9.50 (br s, 1H), 8.78 (br s, 1H), 8.63 (br s, 1H), 8.54 (br s, 1H), 7.81 (br m, 2H), 7.54 (br m, 2H), 7.27 (br m, 9H), 6.82 (br s, 1H), 5.76 (br s, 1H), 3.41 (br s, 3H), 2.56 (br s, 2H), 1.16 (br s, 3H). MS (ES+, m/z) 518 (M+H).

Example 7

3-({4-[[4-({[(3-Fluorophenyl)amino]corbonyl}amino)phenyl](methyl)amino]pyrimidin-2-yl}amino)benzenesulfonamide

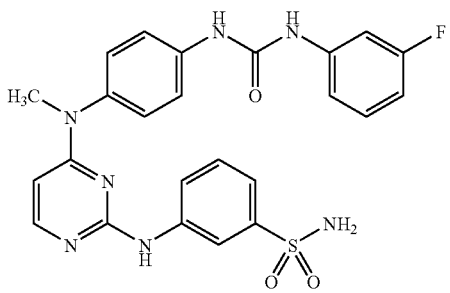

¹H NMR (300 MHz, DMSO-d₆) δ 9.53 (s, 1H), 8.95 (s, 1H), 8.89 (s, 1H), 8.54 (s, 1H), 7.87 (d, J=6.0 Hz, 1H), 7.79 (d, J=7.9 Hz, 1H), 7.24-7.57 (m, 10H), 7.13 (d, J=8.8 Hz, 1H), 6.79 (m, 1H), 5.78 (d, J=6.0 Hz, 1H), 3.43 (s, 3H). MS (ES+, m/z) 508 (M+H).

Example 8

N-(3-Chlorophenyl)-N'-{4-[(2-{[5-(ethylsulfonyl)-2-methoxyphenyl]amino}pyrimidin-4-yl)(methyl)amino]phenyl}urea

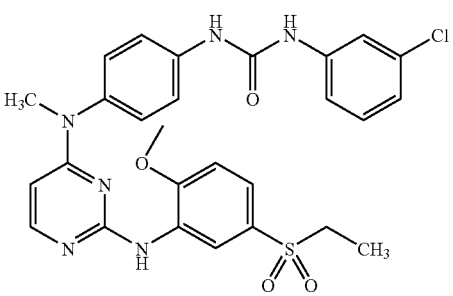

¹H NMR (300 MHz, DMSO-d₆) δ 9.10 (d, J=2.1 Hz, 1H), 8.94 (s, 1H), 8.92 (s, 1H), 7.87 (d, J=6.0 Hz, 1H), 7.78 (s, 1H), 7.71 (s, 1H), 7.57 (d, J=8.8 Hz, 2H), 7.46 (m, 1H), 7.24-7.33 (m, 5H), 7.03 (m, 1H), 5.78 (d, J=6.2 Hz, 1H), 3.99 (s, 3H), 3.44 (s, 3H), 3.19 (q, J=7.3 Hz, 2H), 1.10 (t, J=7.3 Hz, 3H). MS (ES+, m/z) 568 (M+H).

Example 9

3-({4-[[4-({[(3-Chlorophenyl)amino]carbonyl}amino)phenyl](methyl)amino]-pyrimidin-2-yl}amino)benzenesulfonamide

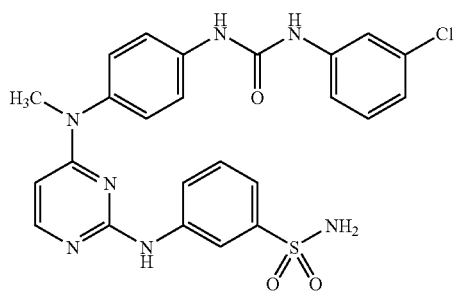

¹H NMR (300 MHz, DMSO-d₆) δ 9.53 (s, 1H), 8.93 (s, 1H), 8.91 (s, 1H), 8.54 (s, 1H), 7.87 (d, J=5.9 Hz, 1H), 7.78 (d, J=7.7 Hz, 1H), 7.71 (s, 1H), 7.56 (d, J=8.6 Hz, 2H), 7.24-7.41 (m, 8H), 7.02 (d, J=6.4 Hz, 1H), 5.78 (d, J=6.0 Hz, 1H), 3.43 (s, 3H). MS (ES+, m/z) 525 (M+H).

Example 10

3-({4-[{4-[(anilinocarbonyl)amino]phenyl}(methyl)amino]pyrimidin-2-yl}amino)benzenesulfonamide

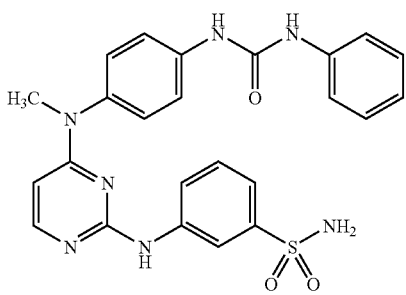

¹H NMR (300 MHz, DMSO-d₆) δ 9.51 (s, 1H), 8.81 (s, 1H), 8.70 (s, 1H), 8.55 (s, 1H), 7.87 (d, J=6.0 Hz, 1H), 7.79 (d, J=7.9 Hz, 1H), 7.56 (d, J=8.6 Hz, 2H), 7.46 (d, J=7.9 Hz, 2H), 7.24-7.41 (m, 8H), 6.97 (t, J=7.4 Hz, 1H), 5.77 (d, J=6.0 Hz, 1H), 3.42 (s, 3H). MS (ES+, m/z) 490 (M+H).

Example 11

3-({4-[{4-[({[2-Fluoro-5-(trifluoromethyl)phenyl]amino}carbonyl)amino]phenyl}(methyl)amino]pyrimidin-2-yl}amino)benzenesulfonamide

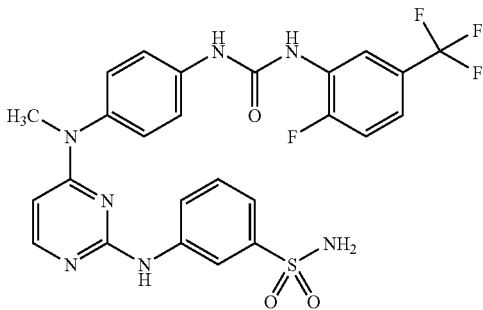

¹H NMR (300 MHz, DMSO-d₆) δ 9.54 (s, 1H), 9.32 (s, 1H), 8.93 (s, 1H), 8.62 (d, J=5.7 Hz, 1H), 8.54 (s, 1H), 7.87 (d, J=5.9 Hz, 1H), 7.78 (d, J=7.6 Hz, 1H), 7.58 (d, J=8.5 Hz, 2H), 7.49 (d, J=10.4 Hz, 1H), 7.24-7.41 (m, 7H), 5.78 (d, J=6.0 Hz, 1H), 3.43 (s, 3H). MS (ES+, m/z) 576 (M+H).

Example 12

N-(3-fluorophenyl)-N'-(4-{methyl[2-({4-[(methylsulfonyl)methyl]phenyl}amino)pyrimidin-4-yl]amino}phenyl)urea hydrochloride

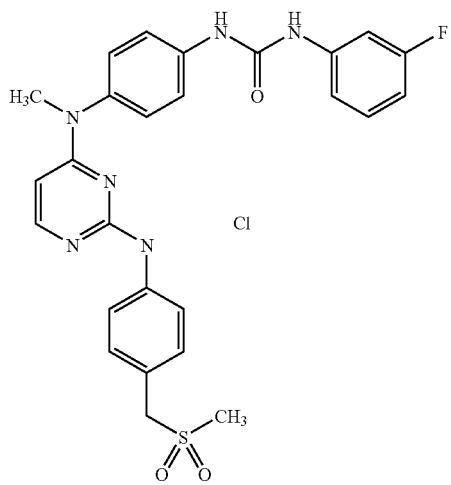

¹H NMR (400 MHz, DMSO-d₆) δ 9.24 (s, 1H), 8.92 (br s, 1H), 8.86 (br s, 1H), 7.85 (d, J=5.8 Hz, 1H), 7.75 (d, J=8.4 Hz, 2H), 7.53 (d, J=8.7 Hz, 2H), 7.48 (m, 1H), 7.26 (m, 5H), 7.12 (d, J=8.1 Hz, 1H), 6.77 (m, 1H), 5.77 (d, J=6.0 Hz, 1H), 4.33 (s, 2H), 3.39 (s, 3H), 2.83 (s, 3H). MS (ES+, m/z) 520 (M+H).

Example 13

N-[2-fluoro-5-(trifluoromethyl)phenyl]-N'-(4-{methyl[2-({4-(methylsulfonyl)methyl]phenyl}amino)pyrimidin-4-yl]amino}phenyl)urea hydrochloride

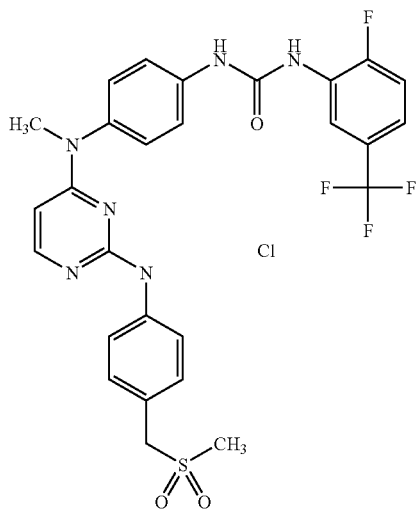

¹H NMR (400 MHz, DMSO-d₆) δ 9.29 (s, 1H), 9.24 (s, 1H), 8.91 (br s, 1H), 8.61 (d, J=7.1 Hz, 1H), 7.86 (d, J=5.8 Hz, 1H), 7.74 (d, J=8.6 Hz, 2H), 7.55 (d, J=8.6 Hz, 2H), 7.49 (m, 1H), 7.39 (m, 1H), 7.26 (d, J=8.8 Hz, 2H), 7.22 (d, J=8.6 Hz, 2H), 5.78 (d, J=6.0 Hz, 1H), 4.32 (s, 2H), 3.40 (s, 3H), 2.83 (s, 3H). MS (ES+, m/z) 588 (M+H).

Example 14

3-({4-[{3-[({[2-Fluoro-5-(trifluoromethyl)phenyl]amino}carbonyl)amino]phenyl}(methyl)amino]pyrimidin-2-yl}amino)benzenesulfonamide

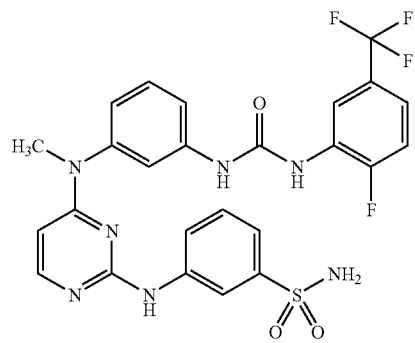

¹H NMR (300 MHz, DMSO-d₆) δ 9.55 (s, 1H), 9.33 (s, 1H), 8.93 (d, J=2.5 Hz, 1H), 8.58 (d, L=7.3 Hz, 1H), 8.54 (s, 1H), 7.91 (d, J=6.0 Hz, 1H), 7.79 (d, J=7.9 Hz, 1H), 7.57 (s, 1H), 7.29-7.53 (m, 6H), 7.24 (s, 2H), 7.01 (d, J=8.2 Hz, 1H), 5.87 (d, J=6.0 Hz, 1H), 3.46 (s, 3H). MS (ES+, m/z) 576 (M+H).

Example 15

3-({4-[[3-({[(3-Chlorophenyl)amino]carbonyl}amino)phenyl](methyl)amino]pyrimidin-2-yl}amino)benzenesulfonamide

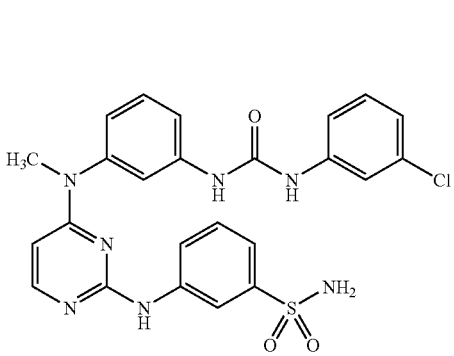

¹H NMR (300 MHz, DMSO-d₆) δ 9.55 (s, 1H), 8.92 (s, 1H), 8.91 (s, 1H), 8.54 (s, 1H), 7.90 (d, J=6.0 Hz, 1H), 7.80 (d, J=7.9 Hz, 1H), 7.70 (s, 1H), 7.53 (s, 1H), 7.25-7.41 (m, 8H), 7.01 (m, 2H), 5.88 (d, J=6.0 Hz, 1H), 3.45 (s, 3H). MS (ES+, m/z) 525 (M+H).

Example 16

3-({4-[[3-({[(3-Fluorophenyl)amino]carbonyl}amino)phenyl](methyl)amino]pyrimidin-2-yl}amino)benzenesulfonamide

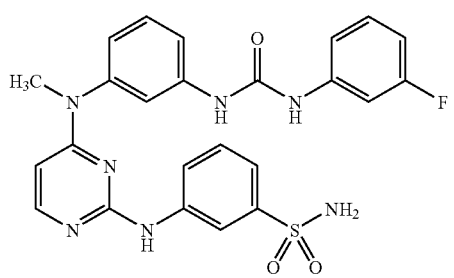

¹H NMR (300 MHz, DMSO-d₆) δ 9.55 (s, 1H), 8.94 (s, 1H), 8.90 (s, 1H), 8.54 (s, 1H), 7.90 (d, J=6.0 Hz, 1H), 7.80 (d, J=7.9 Hz, 1H), 7.53 (s, 1H), 7.28-7.50 (m, 6H), 7.25 (s, 2H), 7.12 (d, J=8.0 Hz, 1H), 6.97 (d, J=7.6 Hz, 1H), 6.78 (m, 1H), 5.88 (d, J=6.0 Hz, 1H), 3.45 (s, 3H). MS (ES+, m/z) 508 (M+H).

Example 17

N-{4-[(2-{[5-(Ethylsulfonyl)-2-methoxyphenyl]amino}pyrimidin-4-yl)(methyl)amino]phenyl}-N'-[2-fluoro-5-(trifluoromethyl)phenyl]urea

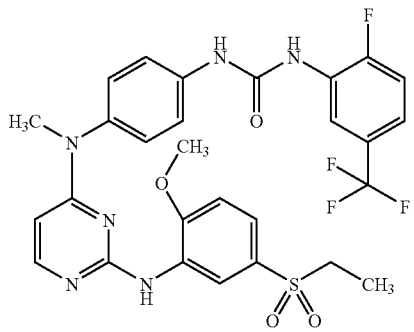

$^1$H NMR (300 MHz, DMSO-$d_6$) δ 9.32 (s, 1H), 9.10 (d, J=2.2 Hz, 1H), 8.94 (d, J=2.8 Hz, 1H), 8.62 (dd, J=7.3 Et 2.0 Hz, 1H), 7.88 (d, J=6.1 Hz, 1H), 7.78 (s, 1H), 7.58 (d, J=8.8 Hz, 2H), 7.24-7.54 (m, 6H), 5.79 (d, J=6.0 Hz, 1H), 3.99 (s, 3H), 3.44 (s, 3H), 3.19 (q, J=7.3 Hz, 2H), 1.10 (t, J=7.3 Hz, 3H). MS (ES+, m/z) 619 (M+H).

Example 18

N-{4-[(2-{[5-(Ethylsulfonyl)-2-methoxyphenyl]amino}pyrimidin-4-yl)(methyl)amino]phenyl}-N'-(3-fluorophenyl)urea

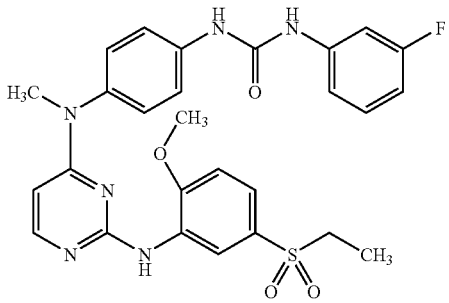

$^1$H NMR (300 MHz, DMSO-$d_6$) δ 9.10 (d, J=2.2 Hz, 1H), 8.96 (s, 1H), 8.91 (s, 1H), 7.87 (d, J=6.0 Hz, 1H), 7.78 (s, 1H), 7.56 (d, J=8.8 Hz, 2H), 7.11-7.49 (m, 7H), 6.79 (m, 1H), 5.78 (d, J=6.0 Hz, 1H), 3.99 (s, 3H), 3.44 (s, 3H), 3.19 (q, J=7.3 Hz, 2H), 1.10 (t, J=7.3 Hz, 3H). MS (ES+, m/z) 551 (M+H).

Example 19

4-({4-[[4-({[(3-chlorophenyl)amino]carbonyl}amino)phenyl](methyl)amino]pyrimidin-2-yl}amino)benzenesulfonamide

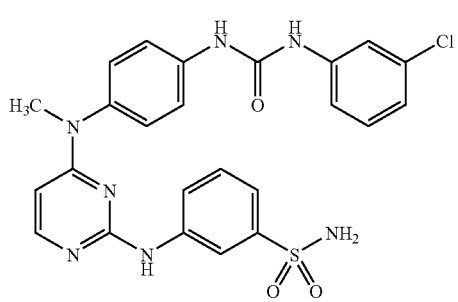

$^1$H NMR (300 MHz, DMSO-$d_6$) δ 9.58 (s, 1H), 8.92 (s, 1H), 8.91 (s, 1H), 7.90 (m, 3H), 7.72 (s, 1H), 7.66 (d. J=8.8 Hz, 2H), 7.57 (d, J=8.7 Hz, 2H), 7.30 (m, 5H), 7.11 (s, 1H), 7.03 (m, 1H), 5.85 (d, J=6.0 Hz, 1H), 3.42 (s, 3H). MS (ES+, m/z) 524 (M+H).

Example 20

4-({4-[[4-({[(3-ethylphenyl)amino]carbonyl}amino)phenyl](methyl)amino]pyrimidin-2-yl}amino)benzenesulfonamide

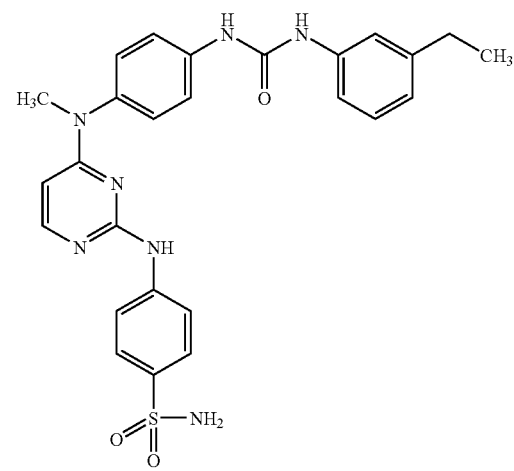

$^1$H NMR (300 MHz, DMSO-$d_6$) δ 9.58 (s, 1H), 8.79 (br s, 1H), 8.64 (br s, 1H), 7.90 (m, 3H), 7.65 (d, J=8.8 Hz, 2H), 7.56 (d, J=8.8 Hz, 2H), 7.47-7.16 (m, 6H), 7.11 (s, 1H), 6.83 (d, J=7.3 Hz, 1H), 5.85 (d, J=6.0 Hz, 1H), 3.41 (s, 3H), 2.57 (m, 2H), 1.18 (m, 3H). MS (ES+, m/z) 517 (M+H).

Example 21

4-{[4-(methyl{4-[({[4-(trifluoromethoxy)phenyl]amino}carbonyl)amino]phenyl}amino)pyrimidin-2-yl]amino}benzenesulfonamide

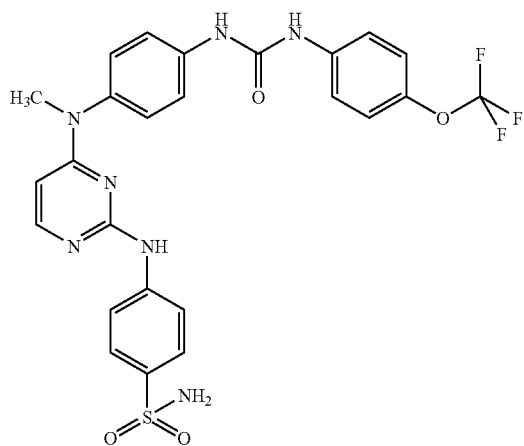

¹H NMR (300 MHz, DMSO-d$_6$) δ 9.58 (s, 1H), 8.92 (br s, 1H), 8.88 (br s, 1H), 7.90 (m, 4H), 7.66 (d, J=8.8 Hz, 2H), 7.57 (m, 4H), 7.28 (m, 4H), 7.11 (s, 1H), 5.86 (d, J=6.0 Hz, 1H), 3.41 (s, 3H). MS (ES+, m/z) 574 (M+H).

Example 22

N-(4-{methyl[2-({3-[(methylsulfonyl)methyl]phenyl}amino)pyrimidin-4-yl]amino}phenyl)-N'-[4-(trifluoromethoxy)phenyl]urea

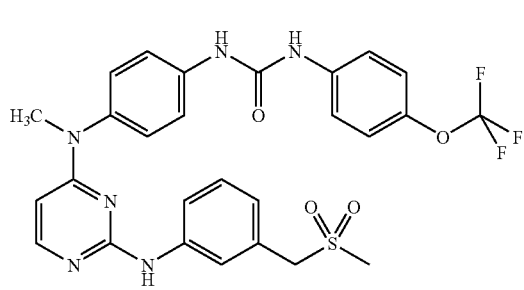

¹H NMR (400 MHz, DMSO-d$_6$) δ 9.22 (br s, 1H), 8.90 (br s, 1H), 8.85 (br s, 1H), 7.85 (m, 2H), 7.67 (d, J=8.1 Hz, 1H), 7.56-7.53 (m, 4H), 7.29-7.18 (m, 5H), 6.90 (d, J=7.3 Hz, 1H), 5.77 (d, J=5.9 Hz, 1H), 4.35 (br s, 2H), 3.39 (s, 3H), 2.89 (s, 3H). MS (ES+, m/z) 587 (M+H).

Example 23

N-(2,3-dihydro-1H-inden-5-yl)-N'-(4-{methyl[2-({3-[(methylsulfonyl)methyl]phenyl}amino)pyrimidin-4-yl]amino}phenyl)urea

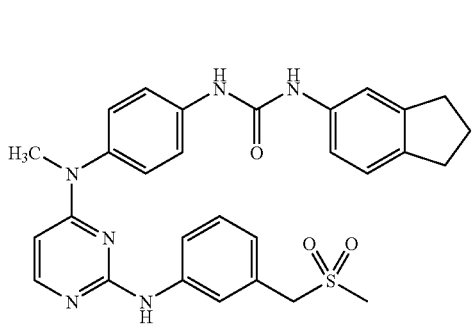

¹H NMR (400 MHz, DMSO-d$_6$) δ 9.21 (br s, 1H), 8.72 (br s, 1H), 8.53 (br s, 1H), 7.85-7.83 (m, 2H), 7.68 (d, J=8.2 Hz, 1H), 7.52 (d, J=8.8 Hz, 2H), 7.37 (br s, 1H), 7.22-7.08 (m, 5H), 6.90 (d, J=7.7 Hz, 1H), 5.76 (d, J=6.0 Hz, 1H), 4.35 (br s, 2H), 3.39 (s, 3H), 2.89 (s, 3H), 2.83-2.75 (m, 4H), 1.98-1.94 (m, 2H). MS (ES+, m/z) 543 (M+H).

Example 24

N-butyl-N'-(4-{methyl[2-({3-[(methylsulfonyl)methyl]phenyl}amino)pyrimidin-4-yl]amino}phenyl)urea

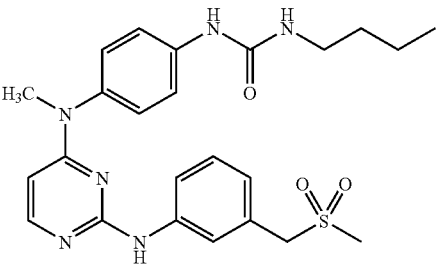

¹H NMR (300 MHz, DMSO-d$_6$) δ 9.22 (br s, 1H), 8.53 (br s, 1H), 7.85-7.83 (m, 2H), 7.69 (d, J=8.5 Hz, 1H), 7.48 (d, J=8.8 Hz, 2H), 7.25-7.15 (m, 3H), 6.92 (d, J=7.7 Hz, 1H), 6.14 (t, J=5.7 Hz, 1H), 5.73 (d, J=6.0 Hz, 1H), 4.36 (br s, 2H), 3.38 (s, 3H), 3.12-3.05 (m, 2H), 2.91 (s, 3H), 1.46-1.27 (m, 4H), 0.90 (t, J=7.2 Hz, 3H). MS (ES+, m/z) 483 (M+H).

Example 25

4-({4-[[4-({[(3-fluorophenyl)amino]carbonyl}amino)phenyl](methyl)amino]pyrimidin-2-yl}amino)benzenesulfonamide

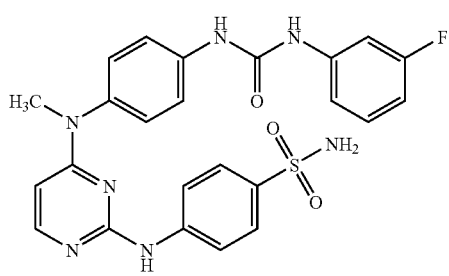

¹H NMR (300 MHz, DMSO-d₆) δ 9.58 (br s, 1H), 8.94 (br s, 1H), 8.89 (br s, 1H), 7.92-7.88 (m, 3H), 7.67 (d, J=0.8 Hz, 2H), 7.58-7.48 (m, 3H), 7.35-7.25 (m, 4H), 7.15-7.11 (m, 2H), 6.79 (m, 1H), 5.86 (d, J=6.0 Hz, 1H), 3.42 (s, 3H). MS (ES+, m/z) 508 (M+H).

Example 26

4-({4-[[4-({[(3-chlorophenyl)amino]carbonyl}amino)phenyl](methyl)amino]pyrimidin-2-yl}amino)benzenesulfonamide

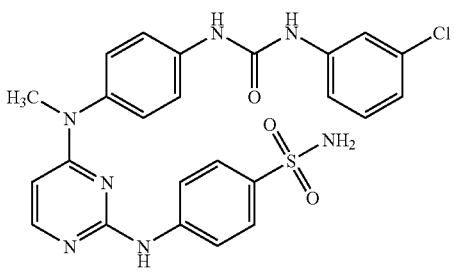

¹H NMR (300 MHz, DMSO-d₆) δ 9.58 (br s, 1H), 8.92-8.91 (m, 2H), 7.92-7.88 (m, 3H), 7.72 (br s, 1H), 7.66 (d, J=8.8 Hz, 2H), 7.57 (d, J=8.8 Hz, 2H), 7.31-7.25 (m, 4H), 7.11 (br s, 2H), 7.03 (m, 1H), 5.85 (d, J=6.0 Hz, 1H), 3.42 (s, 3H). MS (ES+, m/z) 525 (M+H).

Example 27

4-({4-[{4-[({[2-fluoro-5-(trifluoromethyl)phenyl]amino}carbonyl)amino]phenyl}(methyl)amino]pyrimidin-2-yl}amino)benzenesulfonamide

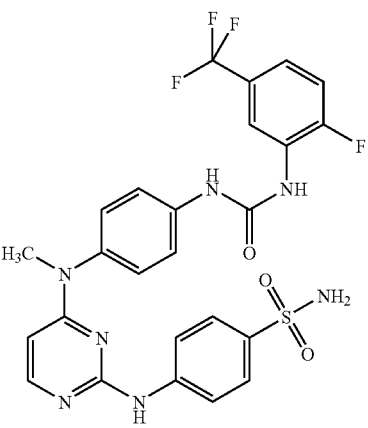

¹H NMR (300 MHz, DMSO-d₆) δ 9.58 (br s, 1H), 9.32 (br s, 1H), 8.93 (m, 1H), 8.64-8.62 (m, 2H), 7.93-7.87 (m, 3H), 7.66-7.41 (m, 6H), 7.30-7.28 (m, 2H), 7.11 (br s, 1H), 5.86 (d, J=6.0 Hz, 1H), 3.42 (s, 3H). MS (ES+, m/z) 576 (M+H).

Example 28

4-{[4-(methyl{4-[({[4-(trifluoromethyl)phenyl]amino}carbonyl)amino]phenyl}amino)pyrimidin-2-yl]amino}benzenesulfonamide

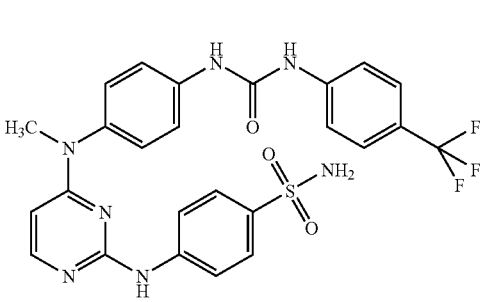

¹H NMR (300 MHz, DMSO-d₆) δ 9.58 (br s, 1H), 9.14 (br s, 1H), 8.96 (br s, 1H), 7.93-7.88 (m, 3H), 7.69-7.56 (m, 8H), 7.28 (d, J=8.7 Hz, 2H), 7.11 (br s, 2H), 5.86 (d, J=6.0 Hz, 1H), 1.42 (s, 3H). MS (ES+, m/z) 558 (M+H).

Example 29

N-[4-(benzyloxy)phenyl]-N'-(4-{methyl[2-({4-[(methylsulfonyl)methyl]phenyl}amino)pyrimidin-4-yl]amino}phenyl)urea

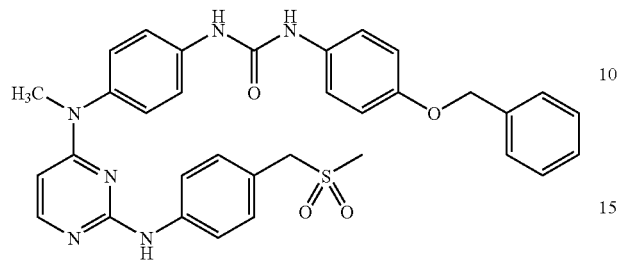

$^1$H NMR (300 MHz, DMSO-d$_6$) δ 9.24 (br s, 1H), 8.73 (br s, 1H), 8.51 (br s, 1H), 7.86 (d, J=6.0 Hz, 1H), 7.77 (d, J=8.5 Hz, 2H), 7.54 (d, J=8.9 Hz, 2H), 7.45-7.31 (m, 7H), 7.25-7.22 (m, 4H) 6.96 (d, J=8.9 Hz, 2H), 5.78 (d, J=6.0 Hz, 1H), 5.06 (s, 2H), 4.34 (s, 2H), 3.40 (s, 3H), 2.85 (s, 3H). MS (ES+, m/z) 609 (M+H).

Example 30

N-(4-fluorophenyl)-N'-(4-{methyl[2-({4-[(methylsulfonyl)methyl]phenyl}amino) pyrimidin-4-yl]amino}phenyl)urea

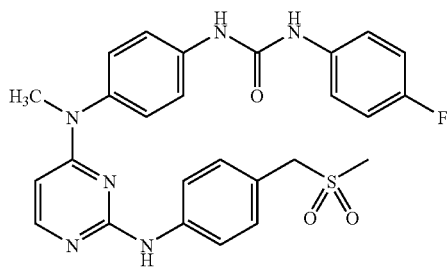

$^1$H NMR (300 MHz, DMSO-d$_6$) δ 9.25 (br s, 1H), 8.80 (br s, 1H), 8.73 (br s, 1H), 7.86 (d, J=6.0 Hz, 1H), 7.77 (d, J=8.5 Hz, 2H), 7.55 (d, J=8.5 Hz, 2H), 7.50-7.45 (m, 3H), 7.26-7.23 (m, 3H) 7.15-7.09 (m, 2H), 5.78 (d, J=6.0 Hz, 1H), 4.34 (s, 2H), 3.40 (s, 3H), 2.85 (s, 3H). MS (ES+, m/z) 521 (M+H).

Example 31

N-(4-{methyl[2-({3-[(methylsulfonyl)methyl]phenyl}amino)pyrimidin-4-yl]amino}phenyl)-N'-(2-phenylethyl)urea

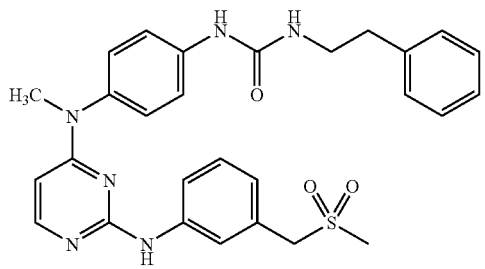

$^1$H NMR (400 MHz, DMSO-d$_6$) δ 9.21 (br s, 1H), 8.61 (br s, 1H), 7.83-7.81 (m, 2H), 7.67 (d, J=8.4 Hz, 1H), 7.46 (d, J=8.6 Hz, 2H), 7.32-7.14 (m, 8H), 6.90 (d, J=7.5 Hz, 1H), 6.13 (t, J=5.7 Hz, 1H), 5.72 (d, J=6.0 Hz, 1H), 4.35 (s, 2H), 3.36 (s, 3H), 3.34-3.28 (m, 2H), 2.89 (s, 3H), 2.74 (t, J=7.2 Hz, 2H). MS (ES+, m/z) 531 (M+H).

Example 32

N-(4-{methyl[2-({3-[(methylsulfonyl)methyl]phenyl}amino)pyrimidin-4-yl]amino}phenyl)-N'-propylurea

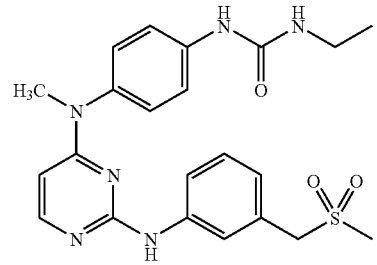

$^1$H NMR (400 MHz, DMSO-d$_6$) δ 9.21 (br s, 1H), 8.54 (br s, 1H), 7.82 (d, J=6.1 Hz, 2H), 7.67 (d, J=7.9 Hz, 1H), 7.46 (d, J=8.8 Hz, 2H), 7.22-7.14 (m, 3H), 6.91 (m, 1H), 6.11 (t, J=5.7 Hz, 1H), 5.72 (d, J=6.0 Hz, 1H), 4.35 (s, 2H), 3.36 (s, 3H), 3.10 (m, 2H), 2.89 (s, 3H), 1.03 (t, J=7.2 Hz, 3H). MS (ES+, m/z) 455 (M+H).

Example 33

N-(2,6-dichlorophenyl)-N'-(4-{methyl[2-({3-[(methylsulfonyl)methyl]phenyl}mino)pyrimidin-4-yl]amino}phenyl)urea

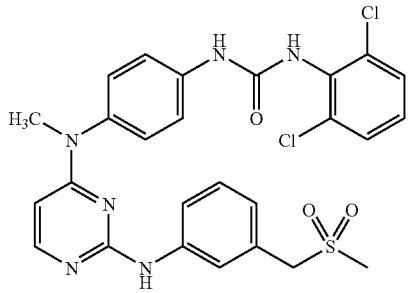

$^1$H NMR (300 MHz, DMSO-d$_6$) δ 9.23 (br s, 1H), 9.11 (br s, 1H), 8.25 (br s, 1H), 7.86-7.84 (m, 2H), 7.69 (d, J=8.4 Hz, 1H), 7.57-7.53 (m, 4H), 7.33 (t, J=8.1 Hz, 1H), 7.25-7.19 (m, 3H), 6.92 (d, J=7.5 Hz, 1H), 5.78 (d, J=6.0 Hz, 1H), 4.37 (s, 2H), 3.40 (s, 3H), 2.91 (s, 3H). MS (ES+, m/z) 571 (M+H).

Example 34

N-(4-acetylphenyl)-N'-(4-{methyl[2-({3-[(methyl-sulfonyl)methyl]phenyl}mino)pyrimidin-4-yl]amino}phenyl)urea

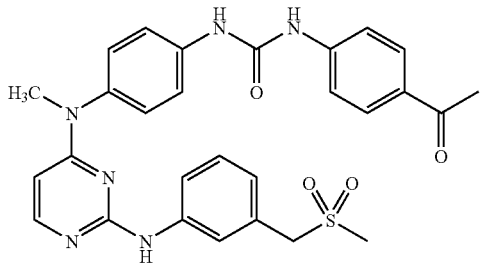

$^1$H NMR (300 MHz, DMSO-d$_6$) δ 9.24 (br s, 1H), 9.14 (br s, 1H), 8.95 (br s, 1H), 7.93-7.85 (m, 4H), 7.69 (d, J=8.2 Hz, 1H), 7.61-7.55 (m, 4H), 7.28-7.20 (m, 3H), 6.92 (d, J=7.4 Hz, 1H), 5.79 (d, J=6.0 Hz, 1H), 4.36 (s, 2H), 3.41 (s, 3H), 2.91 (s, 3H), 2.52 (s, 3H). MS (ES+, m/z) 545 (M+H).

Example 35

N-(4-{methyl[2-({3-[(methylsulfonyl)methyl]phenyl}amino)pyrimidin-4-yl]amino}phenyl)-N'-phenylurea

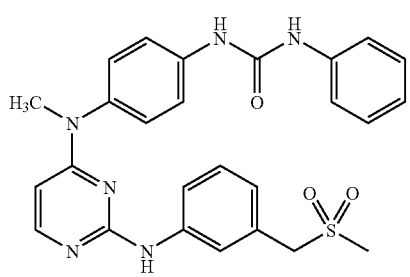

$^1$H NMR (400 MHz, DMSO-d$_6$) δ 9.25 (s, 1H), 8.82 (s, 1H), 8.71 (s, 1H), 7.86 (m, 2H), 7.70 (d, 1H), 7.56 (d, 2H), 7.47 (d, 2H), 7.26 (m, 5H), 6.98 (t, 1H), 6.93 (d, 1H), 5.78 (d, 1H), 4.38 (s, 2H), 3.33 (s, 3H), 2.92 (s, 3H). MS (ES+, m/z) 503 (M+H).

Example 36

N-methyl-N-(4-{methyl[2-({3-[(methylsulfonyl)methyl]phenyl}amino)pyrimidin-4-yl]amino}phenyl)-N'-phenylurea

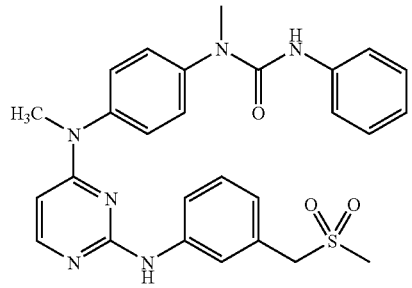

$^1$H NMR (400 MHz, DMSO-d$_6$) δ 9.28 (s, 1H), 8.28 (s, 1H), 7.89 (d, 1H), 7.85 (s, 1H), 7.71 (d, 1H), 7.50-7.31 (m, 6H), 7.30-7.13 (m, 3H), 6.93 (m, 2H), 5.93 (d, 1H), 4.38 (s, 2H), 3.45 (s, 3H), 3.31 (s, 3H), 2.91 (s, 3H). MS (ES+, m/z) 517 (M+H).

Example 37

N-[2-(dimethylamino)ethyl]-N'-(4-{methyl[2-({3-[(methylsulfonyl) ethyl]phenyl}amino)pyrimidin-4-yl]amino}phenyl)urea

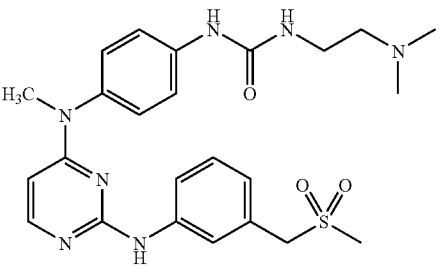

To a solution of 1,1'-carbonyldiimidazole (420.3 mg, 2.592 mmol) in N,N-dimethylacetamide (6 mL) was added Intermediate Example 6 (331 mg, 0.864 mmol). The mixture was stirred for 24 h and then N,N-dimethylethane-1,2-diamine (0.019 mL, 1.728 mmol) was added. The mixture was stirred for 2 h. The reaction was quenched with saturated sodium bicarbonate solution (30 mL) and the product precipitated. The crude product was filtered, washed with water, diethyl ether and air dried to give the desired product without further purification. $^1$H NMR (400 MHz, DMSO-d$_6$) δ 9.23 (br s, 1H), 8.80 (br s, 1H), 7.85-7.84 (m, 2H), 7.70 (d, J=7.8 Hz, 1H), 7.48 (d, J=8.8 Hz, 2H), 7.25-7.16 (m, 3H), 6.92 (d, J=7.7 Hz, 1H), 6.12 (t, J=5.2 Hz, 1H), 5.78 (d, J=5.9 Hz, 1H), 4.37 (br s, 2H), 3.39 (br s, 3H), 3.19 (m, 2H), 2.92 (br s, 3H), 2.33 (t, J=6.1 Hz, 2H), 2.18 (br s, 6H). MS (ES+, m/z) 498 (M+H).

Unless otherwise indicated, the compounds of Examples 38-45 were prepared according to the general procedures set forth above in Example 37.

Example 38

N-cyclohexyl-N'-(4-{methyl[2-({3-[(methylsulfonyl)methyl]phenyl}amino)pyrimidin-4-yl]amino}phenyl)urea

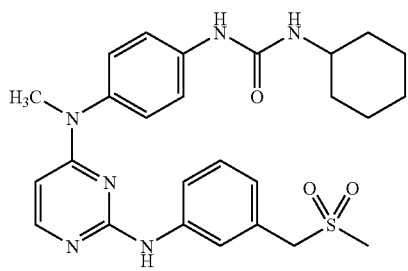

$^1$H NMR (300 MHz, DMSO-d$_6$) δ 9.22 (br s, 1H), 8.43 (br s, 1H), 7.85-7.83 (m, 2H), 7.69 (d, J=8.3 Hz, 1H), 7.46 (d, J=8.7 Hz, 2H), 7.25-7.15 (m, 3H), 6.92 (d, J=7.6 Hz, 1H), 6.10 (d, J=7.8 Hz, 1H), 5.73 (d, J=5.9 Hz, 1H), 4.36 (s, 2H), 3.38 (s, 3H), 2.91 (s, 3H), 1.78 (m, 2H), 1.64 (m, 2H), 1.53 (m, 1H), 1.33-1.15 (m, 6H). MS (ES+, m/z) 509 (M+H).

Example 39

N-(4-{methyl[2-({3-[(methylsulfonyl)methyl]phenyl}amino)pyrimidin-4-yl]amino}phenyl)-N'-propylurea

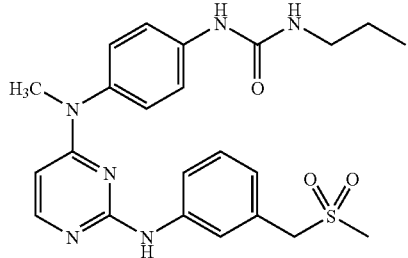

$^1$H NMR (300 MHz, DMSO-d$_6$) δ 9.22 (br s, 1H), 8.55 (br s, 1H), 7.85-7.83 (m, 2H), 7.70 (d, J=8.5 Hz, 1H), 7.48 (d, J=8.7 Hz, 2H), 7.25-7.15 (m, 3H), 6.92 (d, J=7.6 Hz, 1H), 6.18 (t, J=5.7 Hz, 1H), 5.74 (d, J=6.0 Hz, 1H), 4.36 (s, 2H), 3.39 (s, 3H), 3.08-3.02 (m, 2H), 2.91 (s, 3H), 1.50-1.39 (m, 2H), 0.88 (t, J=7.4 Hz, 3H). MS (ES+, m/z) 469 (M+H).

Example 40

N-isopropyl-N'-(4-{methyl[2-({3-[(methylsulfonyl)methyl]phenyl}amino)pyrimidin-4-yl]amino}phenyl)urea

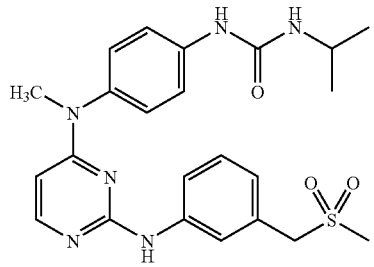

$^1$H NMR (300 MHz, DMSO-d$_6$) δ 9.22 (br s, 1H), 8.42 (br s, 1H), 7.85-7.83 (m, 2H), 7.70 (d, J=8.2 Hz, 1H), 7.47 (d, J=8.6 Hz, 2H), 7.25-7.15 (m, 3H), 6.92 (d, J=7.4 Hz, 1H), 6.03 (d, J=7.5 Hz, 1H), 5.73 (d, J=6.0 Hz, 1H), 4.37 (s, 2H), 3.77 (m, 1H), 3.41 (s, 3H), 2.91 (s, 3H), 1.11-1.09 (m, 6H). MS (ES+, m/z) 469 (M+H).

Example 41

N-(tert-butyl)-N'-(4-{methyl[2-({3-[(methylsulfonyl)methyl]phenyl}amino)pyrimidin-4-yl]amino}phenyl)urea

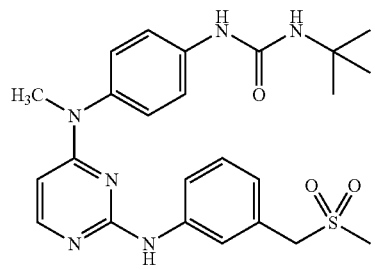

$^1$H NMR (300 MHz, DMSO-d$_6$) δ 9.22 (br s, 1H), 8.38 (br s, 1H), 7.85-7.83 (m, 2H), 7.69 (d, J=7.6 Hz, 1H), 7.44 (d, J=8.5 Hz, 2H), 7.25-7.14 (m, 3H), 6.92 (d, J=7.5 Hz, 1H), 6.02 (br s, 1H), 5.73 (d, J=6.0 Hz, 1H), 4.36 (s, 2H), 3.38 (s, 3H), 2.91 (s, 3H), 1.29 (br s, 9H). MS (ES+, m/z) 483 (M+H).

Example 42

N-[3-({4-[[4-({[(3-chlorophenyl)amino]carbonyl}amino)phenyl](methyl)amino]yrimidin-2-yl}amino)benzyl]methanesulfonamide

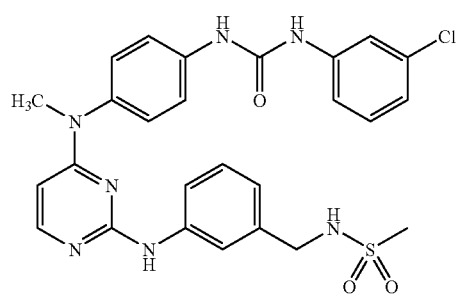

$^1$H NMR (400 MHz, DMSO-d$_6$) δ 9.10 (br s, 1H), 9.06 (br s, 1H), 7.83-7.80 (m, 2H), 7.69 (br s, 1H), 7.54-7.48 (m, 4H), 7.30-7.16 (m, 6H), 7.01-6.98 (m, 1H), 6.85 (m, 1H), 5.74 (m, 1H), 4.05 (m, 2H), 3.39 (s, 3H), 2.91 (s, 3H). MS (ES+, m/z) 552 (M+H).

Example 43

2-[4-({4-[(4-{[(ethylamino)carbonyl]amino}phenyl)(methyl)amino]pyrimidin-2-yl}amino)phenyl]-N-methylethanesulfonamide

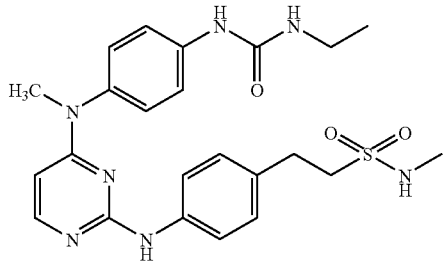

$^1$H NMR (300 MHz, DMSO-d$_6$) δ 9.07 (br s, 1H), 8.72 (br s, 1H), 7.82 (d, J=5.9 Hz, 1H), 7.67 (d, J=8.3 Hz, 2H), 7.48 (d, J=8.5 Hz, 2H), 7.17-7.10 (m, 4H), 6.94 (br s, 1H), 6.24 (br s, 1H), 5.72 (d, J=6.0 Hz, 1H), 3.37-2.83 (m, 9H), 2.59 (br s, 3H), 1.05 (t, J=7.1 Hz, 3H). MS (ES+, m/z) 484 (M+H).

Example 44

N-(4-{methyl[2-({4-[(methylsulfonyl)methyl]phenyl}amino)pyrimidin-4-yl]amino}phenyl)-N'-{4-[(4-methylpiperazin-1-yl)methyl]phenyl}urea

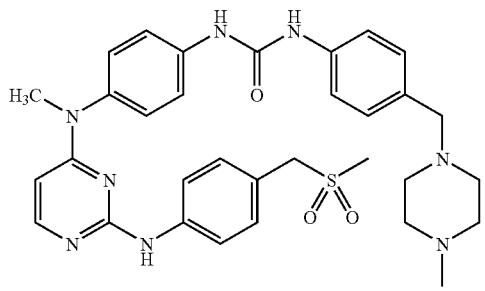

$^1$H NMR (400 MHz, DMSO-d$_6$) δ 9.23 (br s, 1H), 8.77 (br s, 1H), 8.65 (br s, 1H), 7.84 (m, 1H), 7.74 (d, J=8.4 Hz, 2H), 7.56-7.51 (m, 2H), 7.37 (d, J=8.5 Hz, 2H), 7.25-7.15 (m, 6H), 5.76 (d, J=5.8 Hz, 1H), 4.32 (br s, 2H), 3.38-3.28 (m, 5H), 2.82 (br s, 3H), 2.47-2.30 (m, 8H), 2.11 (brs, 3H). MS (ES+, m/z) 615 (M+H).

Example 45

N-(4-{methyl[2-({4-[(methylsulfonyl)methyl]phenyl}amino)pyrimidin-4-yl]amino}phenyl)-N'-{4-[(4-methylpiperazin-1-yl)carbonyl]phenyl}urea

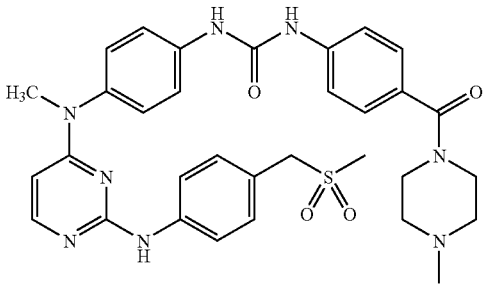

$^1$H NMR (300 MHz, DMSO-d$_6$) δ 9.25 (br s, 1H), 8.89 (br s, 2H), 7.87 (d, J=5.9 Hz, 1H), 7.77 (d, J=8.0 Hz, 2H), 7.56-7.24 (m, 9H), 6.96 (d, J=7.0 Hz, 1H) 5.78 (d, J=5.7 Hz, 1H), 4.34 (br s, 2H), 3.41 (br s, 3H), 2.85 (br s, 3H), 2.30-2.19 (m, 11H). MS (ES+, m/z) 629 (M+H).

Example 46

Phenyl 4-{methyl[2-({3-[(methylsulfonyl)methyl]phenyl}amino)pyrimidin-4-yl]amino}phenylcarbamate

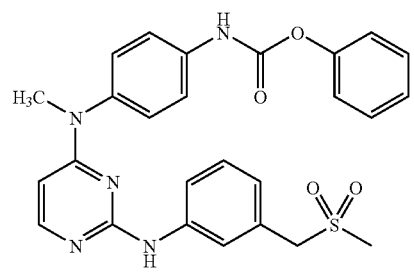

Phenylchloroformate (16 μL, 0.13 mmol) was injected into a stirred solution of Intermediate Example 6 (50 mg, 0.13 mmol) in anhydrous DMF (2 mL). The reaction stirred at room temperature for 1 hour. A saturated aqueous solution of sodium bicarbonate was added drop-wise to the reaction solution resulting in a tan suspension. The suspension was filtered and air-dried. The reaction yielded 45 mg of a tan powder. $^1$H NMR (400 MHz, DMSO-d$_6$) δ 10.38 (s, 1H), 9.23 (s, 1H), 7.84 (d, 2H), 7.66 (d, 1H), 7.58 (d, 2H), 7.42 (t, 2H), 7.30-7.15 (m, 6H), 6.91 (d, 1H), 5.76 (d, 1H), 4.33 (s, 2H), 3.38 (s, 3H), 2.87 (s, 3H). MS (ES+, m/z) 504 (M+H).

Unless otherwise indicated, the compounds of Examples 47-48 were prepared according to the general procedures set forth above in Example 46.

Example 47

Benzyl-4-{methyl[2-({3-[(methylsulfonyl)methyl]phenyl}amino)pyrimidin-4-yl]amino}phenylcarbamate

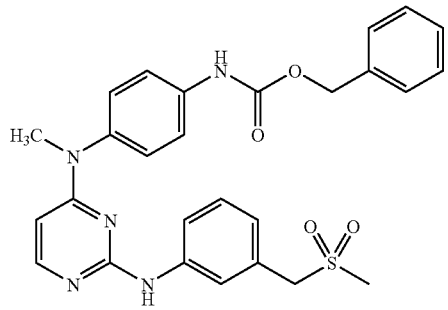

$^1$H NMR (400 MHz, DMSO-d$_6$) δ 9.92 (s, 1H), 9.23 (s, 1H), 7.84 (d, 2H), 7.68 (d, 1H), 7.55 (d, 2H), 7.48-7.31 (m, 5H), 7.29-7.15 (m, 3H), 6.91 (d, 1H), 5.76 (d, 1H), 5.16 (s, 2H), 4.35 (s, 2H), 3.38 (s, 3H), 2.89 (s, 3H). MS (ES+, m/z) 518 (M+H).

Example 48

Phenyl-4-[(2-{[3-(aminosulfonyl)-4-methylphenyl]amino}pyrimidin-4-yl)(methyl) amino]phenylcarbamate

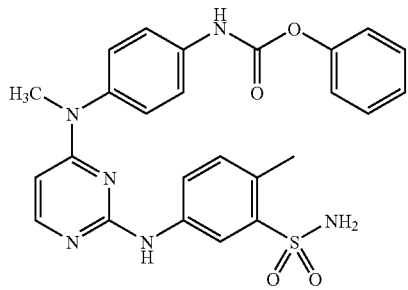

$^1$H NMR (400 MHz, DMSO-d$_6$) δ 10.38 (s, 1H), 9.38 (s, 1H), 8.55 (s, 1H), 7.84 (d, 1H), 7.71 (d, 1H), 7.60 (d, 2H), 7.44 (t, 2H), 7.30-7.10 (m, 8H), 5.73 (d, 1H), 3.42 (s, 3H), 3.31 (s, 3H). MS (ES+, m/z) 505 (M+H).

Example 49

N-(4-{methyl[2-({3-[(methylsulfonyl)methyl]phenyl}amino)pyrimidin-4-yl]amino}phenyl)-1-phenylmethonesulfonamide

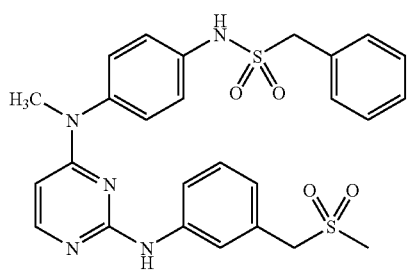

Phenylmethanesulfonyl chloride (20 mg, 0.10 mmol) was added to a stirred solution of Intermediate Example 6 (30 mg, 0.07 mmol) in anhydrous DMF (2 mL). The reaction stirred at room temperature for 15 hrs. Saturated aqueous sodium bicarbonate was added drop-wise until the reaction became a tan suspension. The suspension aggregated into a yellow oil with continued stirring. The reaction product was partitioned between ethyl acetate and distilled water. The organic fraction was dried over magnesium sulfate, filtered and concentrated under vacuum. The crude oil was purified by silica gel chromatography (1-2% methanol/methylene chloride) and lyophylized (acetonitrile/water) to yield 9 mg of a white solid. $^1$H NMR (400 MHz, DMSO-d$_6$) δ 9.98 (s, 1H), 9.26 (s, 1H), 7.88 (d, 1H), 7.83 (s, 1H), 7.70 (d, 1H), 7.34 (m, 3H), 7.32-7.18 (m, 6H), 6.92 (d 1H), 5.78 (d, 1H), 4.52 (s, 2H), 4.37 (s, 2H), 3.40 (s, 3H), 3.15 (d, 1H), 2.90 (s, 3H). MS (ES+, m/z) 538 (M+H).

Example 50

N-(4-{methyl[2-({3-[(methylsulfonyl)methyl]phenyl}amino)pyrimidin-4-yl]amino}phenyl)-2-phenylacetamide

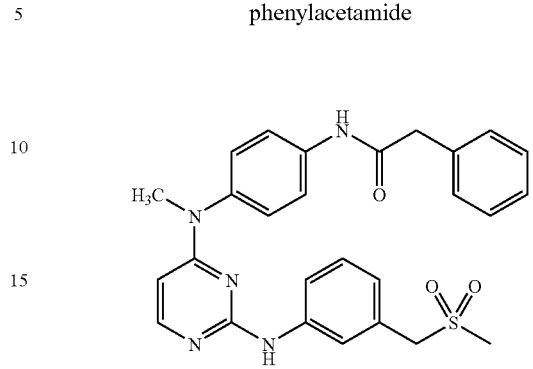

Phenylmethaneacetyl chloride (22 uL, 0.17 mmol) and diisopropylethylamine (23 μL, 0.13 mmol) were added to a stirred solution of Intermediate Example 6 (50 mg, 0.13 mmol) in methylene chloride (2 mL). The reaction stirred at room temperature for 1 hour. The reaction was concentrated to a residue and purified by silica gel chromatography (Gradient: 60-100% ethyl acetate/hexanes). Trituration of the purified fractions (1:1 ethyl acetate/hexanes) produced a white suspension, which was filtered and yielded 12 mg of a white solid. $^1$H NMR (400 MHz, DMSO-d$_6$) δ 10.31 (s, 1H), 9.23 (s, 1H), 7.85 (d, 1H), 7.82 (s, 1H), 7.68 (m, 3H), 7.34 (m, 4H), 7.25 (d, 3H), 7.20 (t, 1H), 6.90 (d, 1H), 5.78 (d, 1H), 4.34 (s, 2H), 3.65 (s, 2H), 3.39 (s, 3H), 2.89 (s, 3H). MS (ES+, m/z) 502 (M+H).

Example 51

N-(4-{methyl[2-({3-[(methylsulfonyl)methyl]phenyl}amino)pyrimidin-4-yl]amino}phenyl)-N'-phenylthiourea

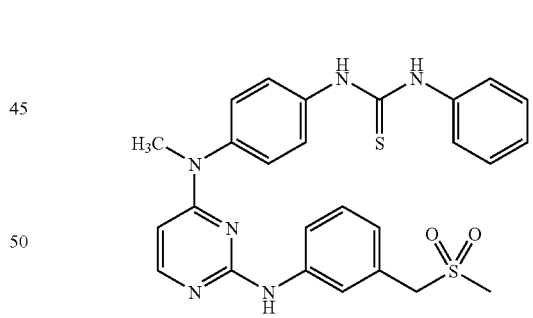

Phenylisothiocyanate (16 μL, 0.13 mmol) was injected into a stirred solution of Intermediate Example 6 (50 mg, 0.13 mmol) in anhydrous DMF (2 mL). The reaction stirred at room temperature for 4 hr and was then diluted in 4 mL 2N ammonia in methanol. A saturated aqueous solution of sodium bicarbonate was added drop-wise to the reaction solution resulting in a white suspension. The suspension was filtered, washed with water and air-dried. The reaction yielded 22 mg of a white powder. $^1$H NMR (400 MHz, DMSO-d$_6$) δ 9.90 (d, 2H), 9.29 (s, 1H), 7.88 (d, 1H), 7.83 (s, 1H), 7.70 (d, 1H), 7.59 (d, 2H), 7.48 (d, 2H), 7.38-7.18 (m, 5H), 7.13 (t, 1H), 6.94 (d, 1H), 5.82 (d, 1H), 4.38 (s, 2H), 3.42 (s, 3H), 2.91 (s, 3H). MS (ES+, m/z) 519 (M+H).

Example 52

N-(4-{methyl[2-({3-[(methylsulfonyl)methyl]phenyl}amino)pyrimidin-4-yl]amino}phenyl)-N'-phenylguanidine

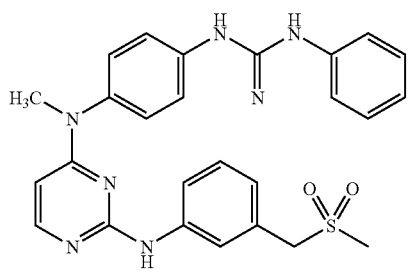

A solution of sodium periodate (22 mg, 0.10 mmol) in distilled water (1 mL) was added drop-wise to a stirred suspension of N-(4-{methyl[2-({3-[(methylsulfonyl)methyl]phenyl}amino)pyrimidin-4-yl]amino}phenyl)-N-phenylthiourea (40 mg, 0.08 mmol), anhydrous DMF (1 mL), distilled water (1 mL) and ammonium hydroxide (15 uL, 30% in water). The reaction was heated to 80° C. for one hour. The reaction was cooled to room temperature. Sodium hydroxide (2 mL, 1N) was added and the reaction stirred for 30 min. The reaction was partitioned between water and methylene chloride and the organic fraction was dried over sodium sulfate. The organic was concentrated under vacuum and the residue was purified by silica gel chromatography (Gradient: first, 60-100% ethyl acetate/hexanes, then, 0-15% methanol/ethyl acetate). The fractions containing the desired product were combined, concentrated and lyophilized (acetonitrile/water). Purification/lyophylization provided 15 mg of an off-white solid. $R_f$=0.05 (10% methanol/ethyl acetate). $^1$H NMR (400 MHz, DMSO-$d_6$) δ 9.23 (s, 1H), 8.31 (br.s, 1H), 8.16 (br.s, 1H), 7.88 (s, 1H), 7.83 (d, 2H), 7.70 (d, 1H), 7.58 (br.s, 1H), 7.24 (m, 3H), 7.16 (d, 2H), 7.03-6.74 (m, 3H), 5.80 (br.s, 1H), 5.22 (br.s, 1H), 5.12 (br.s, 1H), 4.38 (s, 2H), 3.41 (s, 3H), 2.92 (s, 3H). MS (ES+, m/z) 502 (M+H).

Biological Data

Tie2 Fluorescence Polarization Kinase Activity Assay: (TIE2-FP)

Activation of Recombinant Tie2 Activation:

Recombinant GST-Tie2 was activated by incubating the enzyme in 20 mM Tris-HCl, pH 7.5, 12 mM MgCl$_2$, 100 mM NaCl, 20 μM sodium vanidate, 1 mM DT and 300 μM ATP at room temperature for 2 hours. The activation mixture was then passed through a NAP-25 desalting column (Pharmacia Biotech cat. no. 17-0852-O$_2$) to remove the free ATP. The activated enzyme was stored as aliquots at −80° C. in 20 mM Tris-HCl, pH 7.5 and 100 mM NaCl.

Assay Conditions:

The final assay conditions were 50 mM HEPES, pH 7.5, 5% DMSO (when screening compounds), 200 μM ATP, 5 mM MgCl$_2$, 1 mM DTT, 50 μM sodium vanidate, 1 nM activated enzyme, and 200 μM peptide. IC$_{50}$'s of compounds were measured under subsaturating ATP (200 μM) and varing concentrations of activated Tie2 and peptide substrate (RF-WKYEFWR-OH; MW 1873 Da, TFA salt). Panvera Anti-phosphotyrosine antibody (Cat#P2840) and PTK Green Tracer (Cat#P2842) were used to detect the phosphorylated peptide. Polarization was measured on a TECAN Polarion in 138-second cycles for 30 minutes at room temperature. IC$_{50}$'s were then determined from the % polarization using normal calculation methods. Results are indicated below.

VEGF-R2 Enzyme Assay VEGF-E)

The VEGF enzyme assay used the LANCE method (Wallac) and GST-VEGFR2, baculovirus expressed recombinant constructs of the intracellular domains of human TIE2 tagged by GST. The method measured the ability of the purified enzymes to catalyse the transfer of the γ-phosphate from ATP onto tyrosine residues in a biotinylated synthetic peptide, (biotin-aminohexyl-EEEEYFELVAKKKK-NH2). This peptide phosphorylation was detected using the following procedure: GST-VEGFR2 was incubated for 40-60 mins at room temperature with 75 μM ATP, 5 mM MgCl2, 0.1 mM DTT, 0.1 mg/mL BSA and the test compound (diluted from a 10 mM stock in DMSO for desired concentration) in 100 mM HEPES buffer. The reaction was stopped by the addition of EDTA (final concentration 50 mM). Streptavidin linked-APC (allophycocyanin, Molecular Probe) and Europium-labeled anti-phosphorylated tyrosile antibody (Wallac) were then added at the final concentration of 15 nM and 1 nM, respectively. The APC signal was measured using an ARVO multilabel counter (Wallac Berthold, Japan). The percent inhibition of activity was calculated relative to blank control wells. The concentration of test compound that inhibits 50% of activity (IC$_{50}$) was interpolated using nonlinear regression (Levernberg-Marquardt) and the equation, $y=Vmax (1-x/(K+x))+Y2$, where "K" was equal to the IC$_{50}$. The IC$_{50}$ values were converted to pIC$_{50}$ values, i.e., −log IC$_{50}$ in Molar concentration. The results are represented in Table 1 below.

VEGF-Driven Cellular Proliferation Assay: BrdU Incorporation Assay (VEGF-C)

Human umbilical cord endothelial cells (HUVEC, Clonetics, CC2519) were passaged in Type I collagen-coated 100-mm petridishes in EGM-MV medium (Clonetics, CC3125) at 37 C in a humidified 5% CO$_2$, 95% air incubator. (HUVEC passaged more than 6 times in vitro were discarded and not subjected to assaying.) The cells were harvested using trypsin/EDTA, counted using a haemocytometer and plated at 5000 cells/well in a Type I-collagen coated 96-well plate (Becton Dickinson, 354407) in M199 medium (Gibco BRL, 12340-030) containing 5% FBS (Hyclone, A 1115-L) and gentamicin (at 50 ug/ml, Gibco BRL). After incubation overnight at 37° C., the media were replaced with 100 ul of M199 serum-free medium containing compounds at various concentrations with 0.6% DMSO and gentamicin. The compounds were diluted in serum-free M199 medium from 10 mM stock solutions prepared in 100% DMSO. After a 30 min incubation at 37° C. the cells were fed with 100 ul of serum-free M199 medium containing gentamicin, 0.2% culture-grade bovine serum albumin (BSA, Sigma A1993) and 20 ng/ml of VEGF (R&D systems, 293-VE) or 0.6 ng/ml of basic FGF (R&D systems, 233-FB), and cultured at 37° C. for another 24 h. The cells were pulsed with bromodeoxyuridine (BrdU at 10 μM in serum-free M199) at 37° C. for an additional 24 h. The incorporation of BrdU into the proliferating HUVEC were analyzed using BrdU Cell Proliferation ELISA (Roche Molecular Biochemicals, 1647229) according to the manufacturer's protocols. The optical density at 450 nm was measured with a multilabel counter (ARVO SX, Wallac). The percent inhibition of cell growth was calculated relative to blank control wells. The concentration of test compound that inhibits 50% of cell growth ($IC_{50}$) was interpolated using nonlinear regression (Levernberg-Marquardt) and the equation, $\gamma=Vmax\,(1-x/(K+x))+Y2$, where "K" was equal to the $IC_{50}$. The $IC_{50}$ values were converted to $pIC_{50}$ values, i.e., $-\log IC_{50}$ in Molar concentration. The results are represented in Table 1 below.

TABLE I

| Ex. No | TIE2-FP | VEGF-E | VEGF-C |
|---|---|---|---|
| 1 | +++ | +++ | +++ |
| 2 | +++ | +++ | +++ |
| 3 | +++ | +++ | +++ |
| 4 | +++ | +++ | +++ |
| 5 | +++ | +++ | +++ |
| 6 | +++ | +++ | +++ |
| 7 | +++ | +++ | +++ |
| 8 | +++ | +++ | +++ |
| 9 | +++ | +++ | +++ |
| 10 | +++ | +++ | +++ |
| 11 | +++ | +++ | +++ |
| 12 | +++ | +++ | +++ |
| 13 | +++ | +++ | +++ |
| 14 | +++ | +++ | +++ |
| 15 | +++ | +++ | +++ |
| 16 | ++ | +++ | +++ |
| 17 | +++ | +++ | +++ |
| 18 | +++ | +++ | +++ |
| 19 | +++ | +++ | +++ |
| 20 | +++ | +++ | +++ |
| 21 | +++ | +++ | +++ |

+ = $pIC_{50}$ of 5.0-6.0;
++ = $pIC_{50}$ of 6.0-7.0;
+++ = $pIC_{50}$ of >7.0;

We claim:

1. A compound of Formula (I):

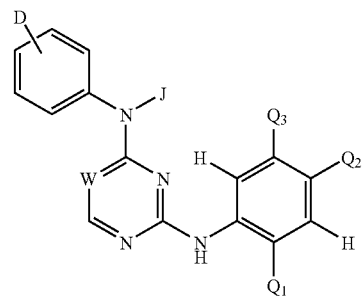

or a salt thereof:

wherein:

W is C—R, wherein R is hydrogen, halogen, or cyano;

J is hydrogen, $C_1$-$C_4$ alkyl, $C_1$-$C_4$ haloalkyl, aralkyl, cyanoalkyl, —$(CH_2)_pC$=$CH(CH_2)_tH$, —$(CH_2)_pC$≡$C(CH_2)_tH$, or $C_3$-$C_7$ cycloalkyl;

p is 1, 2, or 3;

t is 0 or 1;

---

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: peptide substrate

<400> SEQUENCE: 1

Arg Phe Trp Lys Tyr Glu Phe Trp Arg
1               5

<210> SEQ ID NO 2
<211> LENGTH: 14
<212> TYPE: PRT
<213> ORGANISM: Artificial Sequence
<220> FEATURE:
<223> OTHER INFORMATION: biotinylated synthetic peptide

<400> SEQUENCE: 2

Glu Glu Glu Glu Tyr Phe Glu Leu Val Ala Lys Lys Lys Lys
1               5                   10
```

D is

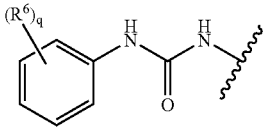

q is 1, 2, or 3;
$Q_1$ is hydrogen, halogen, $C_1$-$C_2$ haloalkyl, $C_1$-$C_2$ alkyl, $C_1$-$C_2$ alkoxy, or $C_1$-$C_2$ haloalkoxy;
$Q_2$ is $A^1$ or $A^2$;
$Q_3$ is $A^1$ when $Q_2$ is $A^2$ and $Q_3$ is $A^2$ when $Q_2$ is $A^1$;
wherein
$A^1$ is hydrogen, halogen, $C_1$-$C_3$ alkyl, $C_1$-$C_3$ haloalkyl, —$OR^1$, and
$A^2$ is the group defined by -$(Z)_m$-$(Z^1)$-$(Z^2)$, wherein
Z is $CH_2$ and m is 0, 1, 2, or 3, or
Z is $NR^2$ and m is 0 or 1, or
Z is O and m is 0 or 1, or
Z is $CH_2NR^2$ and m is 0 or 1;
$Z^1$ is $S(O)_2$, $S(O)$, or $C(O)$; and
$Z^2$ is $C_1$-$C_4$ alkyl, cycloalkyl, heterocyclyl, $NR^3R^4$, aryl, arylamino, aralkyl, aralkoxy, or heteroaryl;
$R^2$, $R^3$, and $R^4$ are each independently selected from hydrogen, hydroxy, alkoxy, aryloxy, aralkoxy, amino, alkylamino, arylamino, aralkylamino, $C_1$-$C_4$ alkyl, $C_3$-$C_7$ cycloalkyl, heterocyclyl, —$S(O)_2R^5$, and —$C(O)R^5$;
$R^5$ is $C_1$-$C_6$ alkyl, or $C_3$-$C_7$ cycloalkyl; and
$R^6$ is the group defined by —$(X_4)_z$—$(X_5)$, wherein
$X_4$ is $C(H)_2$ where z is 0, 1, 2, 3, or 4, and
$X_5$ is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, CN, —$NR^7R^7$, —N(H)C(O)$R^7$, —N(H)C(O)O$R^7$, —N(H)C(O)N$R^7R^7$, N(H)S(O)$_2R^7$, N(H)S(O)$_2$N$R^7R^7$, —OC(O)$R^7$, OC(O)N$R^7R^7$, —C(O)$R^7$, —C(O)N$R^7R^7$, —S$R^7$, —S(O)$R^7$, S(O)$_2R^7R^7$, —or S(O)$_2$N$R^7R^7$; and
$R^7$ is hydrogen, $C_1$-$C_6$ alkyl, $C_1$-$C_2$ haloalkyl, cycloalkyl, heterocyclyl, alkylamino, alkoxy, aryloxy, aralkoxy, arylamino, aralkylamino, aryl or heteroaryl.

2. A compound of formula (II):

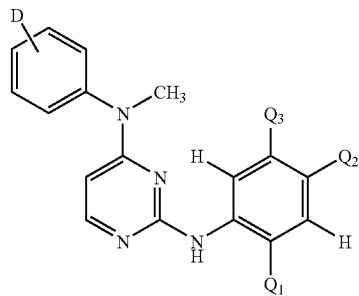

or a salt, thereof:
wherein:
D is

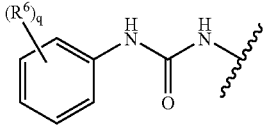

q is 1, 2, or 3;
$Q_1$ is hydrogen, halogen, $C_1$-$C_2$ haloalkyl, $C_1$-$C_2$ alkyl, $C_1$-$C_2$ alkoxy, or $C_1$-$C_2$ haloalkoxy;
$Q_2$ is $A^1$ or $A^2$;
$Q_3$ is $A^1$ when $Q_2$ is $A^2$ and $Q_3$ is $A^2$ when $Q_2$ is $A^1$;
wherein
$A^1$ is hydrogen, halogen, $C_1$-$C_3$ alkyl, $C_1$-$C_3$ haloalkyl, —$OR^1$, and
$A^2$ is the group defined by -$(Z)_m$-$(Z^1)$-$(Z^2)$, wherein
Z is $CH_2$ and m is 0, 1, 2, or 3, or
Z is $NR^2$ and m is 0 or 1, or
Z is O and m is 0 or 1, or
Z is $CH_2NR^2$ and m is 0 or 1;
$Z^1$ is $S(O)_2$, $S(O)$, or $C(O)$; and
$Z^2$ is $C_1$-$C_4$ alkyl, cycloalkyl, heterocyclyl, $NR^3R^4$, arylamino, aralkyl, aralkoxy, or heteroaryl;
$R^2$, $R^3$, and $R^4$ are each independently selected from hydrogen, hydroxy, alkoxy, aryloxy, aralkoxy, amino, alkylamino, arylamino, aralkylamino, $C_1$-$C_4$ alkyl, $C_3$-$C_7$ cycloalkyl, heterocyclyl, —$S(O)_2R^5$, and —$C(O)R^5$;
$R^5$ is $C_1$-$C_6$ alkyl, or $C_3$-$C_7$ cycloalkyl; and
$R^6$ is the group defined by —$(X_4)$, —$(X_5)$, wherein
$X_4$ is $C(H)_2$ where z is 0, 1, 2, 3, or 4, and
$X_5$ is hydrogen, $C_1$-$C_6$ alkyl, $C_1$-$C_6$ haloalkyl, cycloalkyl, heterocyclyl, aryl, heteroaryl, alkoxy, haloalkoxy, hydroxy, aryloxy, aralkoxy, halo, CN, —$NR^7R^7$, —N(H)C(O)$R^7$, —N(H)C(O)O$R^7$, —N(H)C(O)N$R^7R^7$, N(H)S(O)$_2R^7$, N(H)S(O)$_2$N$R^7R^7$, —OC(O)$R^7$, OC(O)N$R^7R^7$, —C(O)$R^7$, —C(O)N$R^7R^7$, —S$R^7$, —S(O)$R^7$, S(O)$_2R^7R^7$-or S(O)$_2$N$R^7R^7$; and
$R^7$ is hydrogen, $C_1$-$C_6$ alkyl, $C_1$-$C_6$ haloalkyl, cycloalkyl, heterocyclyl, alkylamino, alkoxy, aryloxy, aralkoxy, arylamino, aralkylamino, aryl or heteroaryl.

3. A compound as claimed in claim 1, wherein W is C—R and R is hydrogen.

4. A compound as claimed in claim 1, wherein J is hydrogen, $C_1$-$C_4$ alkyl, cyanoalkyl, or —$(CH_2)_p$C≡C$(CH_2)_t$H.

5. A compound as claimed in claim 1, wherein J is hydrogen, methyl, ethyl, isopropyl, cyanomethyl, or —$(CH_2)_p$C≡C$(CH_2)_t$H, wherein p is 1 and t is 0.

6. A compound as claimed in claim 1, wherein J is methyl.

7. A compound as claimed in claim 1, wherein $Q_1$ is hydrogen, halogen, $C_1$-$C_2$ alkyl or $C_1$-$C_2$ alkoxy.

8. A compound as claimed in claim 1, wherein $Q_1$ is hydrogen, chlorine, methyl, or methoxy.

9. A compound as claimed in claim 1, wherein $Q_2$ is $A^2$ and $Q_3$ is $A^1$, wherein $A^1$ is hydrogen, halogen, or $C_1$-$C_3$ haloalkyl and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$-$C_4$ alkyl or $NR^3R^4$ and wherein $R^2$, $R^3$, and $R^4$ are each independently selected from hydrogen, $C_1$-$C_4$alkyl, alkoxy, alkylamino, or amino.

10. A compound as claimed in claim 1, wherein $Q_2$ is $A^2$ and $Q_3$ is $A^1$, wherein $A^1$ is hydrogen or chlorine and $A^2$ is the group defined by $-(Z)_m-(Z^1)(Z^2)$, wherein Z is $CH_2$ and m is 0, 1, 2, or 3; $Z^1$ is $S(O)_2$; and $Z^2$ is $C_1$-$C_4$ alkyl or $NR^3R^4$, wherein $R^3$ and $R^4$ are each independently selected from hydrogen, $C_1$-$C_4$ alkyl, alkoxy, alkylamino, or amino.

11. A compound as claimed in claim 1, wherein $Q_2$ is $A^1$ and $Q_3$ is $A^2$, wherein $A^1$ is hydrogen, halogen, or $C_1$-$C_3$ alkyl and $A^2$ is the group defined by $-(Z)_m-(Z^1)-(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$, $C_4$ alkyl or $NR^3R^4$, and wherein $R^2$, $R^3$, and $R^4$ are each independently selected from hydrogen, $C_1$-$C_4$ alkyl, alkoxy, alkylamino, or amino.

12. A compound as claimed in claim 1, wherein $Q_2$ is $A^1$ and $Q_3$ is $A^2$, wherein $A^1$ is hydrogen, methyl, or chlorine and $A^2$ is the group defined by $-(Z)_m-(Z^1)-(Z^2)$, wherein Z is $CH_2$ and m is 0, 1, 2, or 3; $Z^1$ is $S(O)_2$; and $Z^2$ is $C_1$-$C_4$ alkyl or $NR^3R^4$, wherein $R^3$ and $R^4$ are each independently selected from hydrogen, $C_1$-$C_4$ alkyl, alkoxy, alkylamino, or amino.

13. A compound as claimed in claim 1, selected from the group consisting of:

- 3-{[4-(methyl{4-[({[4-(trifluoromethoxy)phenyl]amino}carbonyl)amino]phenyl}amino) pyrimidin-2-yl]amino}benzenesulfonamide;
- 3-{[4-(methyl{4-[({[4-(trifluoromethyl)phenyl]amino}carbonyl)amino]phenyl}amino) pyrimidin-2-yl]amino}benzenesulfonamide;
- 3-[(4-{methyl[4-({[(4-phenoxyphenyl)amino]carbonyl}amino)phenyl]amino}-pyrimidin-2-yl)amino]benzenesulfonamide;
- 3-[(4-{methyl[4-({[(3-methylphenyl)amino]carbonyl}amino)phenyl]amino}pyrimidin-2-yl)amino]benzenesulfonamide;
- 3-({4-[[4-({[(2-chlorobenzyl)amino]carbonyl}amino)phenyl](methyl)amino]pyrimidin-2-yl}amino)benzenesulfonamide;
- 3-({4-[[4-({[(3-ethylphenyl)amino]carbonyl}amino)phenyl](methyl)amino]pyrimidin-2-yl}amino)benzenesulfonamide;
- 3-({4-[[4-({[(3-fluorophenyl)amino]carbonyl}amino)phenyl](methyl)amino]pyrimidin-2-yl}amino)benzenesulfonamide;
- N-(3-chlorophenyl)-N-{4-[(2-{[5-(ethylsulfonyl)-2-methoxyphenyl]amino}pyrimidin-4-yl)(methyl)amino]phenyl}urea;
- 3-({4-[[4-({[(3-chlorophenyl)amino]carbonyl}amino)phenyl](methyl)amino]-pyrimidin-2-yl}amino)benzenesulfonamide;
- 3-({4-[(4-[(aniline)carbonyl]amino]phenyl](methyl)amino]pyrimidin-2-yl}amino)benzenesulfonamide;
- 3-({4-[{4-[({[2-fluoro-5-(trifluoromethyl)phenyl]amino}carbonyl)amino]phenyl}-(methyl)amino]pyrimidin-2-yl}amino)benzenesulfonamide;
- N-(3-fluorophenyl)-N'-(4-{methyl[2-({4-[(methylsulfonyl)methyl]phenyl]amino) pyrimidin-4-yl]amino}phenyl)urea;
- N-[2-fluoro-5-(trifluoromethyl)phenyl]-N'-(4-{methyl[2-({4-(methylsulfonyl)methyl]phenyl}amino)pyrimidin-4-yl]amino}phenyl)urea;
- 3-({4-[{3-[({[2-fluoro-5-(trifluoromethyl)phenyl]amino}carbonyl)amino]phenyl}-(methyl)amino]pyrimidin-2-yl}amino)benzenesulfonamide;
- 3-({4-[[3-({[(3-chlorophenyl)amino]carbonyl}amino)phenyl](methyl)amino]-pyrimidin-2-yl}amino)benzenesulfonamide;
- 3-({4-[[3-({[(3-fluorophenyl)amino]carbonyl}amino)phenyl](methyl)amino]pyrimidin-2-yl}amino)benzenesulfonamide;
- N-{4-[(2-{[5-(ethylsulfonyl)-2-methoxyphenyl]amino}pyrimidin-4-yl)(methyl)amino]phenyl}-N-[2-fluoro-5-(trifluoromethyl)phenyl]urea;
- N-{4-[(2-{[5-(ethylsulfonyl)-2-methoxyphenyl]amino}pyrimidin-4-yl)(methyl)amino]phenyl}-N-(3-fluorophenyl)urea;
- 4-({4-[[4-({[(3-chlorophenyl)amino]carbonyl}amino)phenyl](methyl)amino]pyrimidin-2-yl}amino)benzenesulfonamide;
- 4-({4-[[4-({[(3-ethylphenyl)amino]carbonyl}amino)phenyl](methyl)amino]pyrimidin-2-yl}amino)benzenesulfonamide;
- 4-{[4-(methyl{4-[({[4-(trifluoromethoxy)phenyl]amino}carbonyl)amino]phenyl-}amino)pyrimidin-2-yl]amino}benzenesulfonamide;
- N-(4-{methyl[2-({3-[(methylsulfonyl)methyl]phenyl}amino)pyrimidin-4-yl]amino}phenyl)-N'-[4-(trifluoromethoxy)phenyl]urea;
- N-(2,3-dihydro-1H-inden-5-yl)-N'-(4-{methyl[2-({3-[(methylsulfonyl)methyl]phenyl}amino)pyrimidin-4-yl]amino}phenyl)urea;
- N-butyl-N'-(4-{methyl[2-({3-[(methylsulfonyl)methyl]phenyl}amino)pyrimidin-4-yl]amino}phenyl)urea;
- 4-({4-[[4-({[(3-fluorophenyl)amino]carbonyl}amino)phenyl](methyl)amino]pyrimidin-2-yl}amino)benzenesulfonamide;
- 4-({4-[[4-({[(3-chlorophenyl)amino]carbonyl}amino)phenyl](methyl)amino]pyrimidin-2-yl}amino)benzenesulfonamide;
- 4-({4-[{4-[({[2-fluoro-5-(trifluoromethyl)phenyl]amino}carbonyl)amino]phenyl}(methyl)amino]pyrimidin-2-yl}amino)benzenesulfonamide;
- 4-{[4-(methyl{4-[({[4-(trifluoromethyl)phenyl]amino}carbonyl)amino]phenyl}amino)pyrimidin-2-yl]amino}benzenesulfonamide;
- N-[4-(benzyloxy)phenyl]-N'-(4-(methyl[2-({4-[(methylsulfonyl)methyl]phenyl})amino)pyrimidin-4-yl]amino}phenyl)urea;
- N-(4-fluorophenyl)-N'-(4-{methyl[2-({4-[(methylsulfonyl)methyl]phenyl}amino) pyrimidin-4-yl]amino}phenyl)urea;
- N-(4-{methyl[2-({3-[(methylsulfonyl)methyl]phenyl}amino)pyrimidin-4-yl]amino}phenyl)-N'-(2-phenylethyl)urea;
- N-(4-{methyl[2-({3-[(methylsulfonyl)methyl]phenyl}amino)pyrimidin-4-yl]amino}phenyl)-N'-propylurea;
- N-(2,6-dichlorophenyl)-N-(4-{methyl[2-({3-[(methylsulfonyl)methyl]phenyl}mino)pyrimidin-4-yl]amino}phenyl)urea;
- N-(4-acetylphenyl)-N'-(4-{methyl[2-({3-[(methylsulfonyl)methyl]phenyl}mino)pyrimidin-4-yl]amino}phenyl)urea;
- N-[2-(dimethylamino)ethyl]-N'-(4-{methyl[2-({3-[(methylsulfonyl) ethyl]phenyl}amino)pyrimidin-4-yl]amino}phenyl)urea;
- N-cyclohexyl-N'-(4-{methyl[2-({3-[(methylsulfonyl)methyl]phenyl}amino)pyrimidin-4-yl]amino}phenyl)urea;
- N-(4-{methyl[2-({3-[(methylsulfonyl)methyl]phenyl}amino)pyrimidin-4-yl]amino}phenyl)-N'-propylurea;

N-isopropyl-N'-(4-{methyl[2-({3-[(methylsulfonyl)methyl]phenyl}amino)pyrimidin-4-yl]amino}phenyl)urea;

N-(tert-butyl)-N'-(4-{methyl[2-({3-[(methylsulfonyl)methyl]phenyl}amino)pyrimidin-4-yl]amino}phenyl)urea;

N-[3-({4-[[4-({[(3-chlorophenyl)amino]carbonyl}amino)phenyl](methyl)amino]pyrimidin-2-yl}amino)benzyl]methanesulfonamide;

2-[4-({4-[(4-{[(ethylamino)carbonyl]amino}phenyl)(methyl)amino]pyrimidin-2-yl}amino)phenyl]-N-methylethanesulfonamide;

N-(4-{methyl[2-({4-[(methylsulfonyl)methyl]phenyl}amino)pyrimidin-4-yl]amino}phenyl)-N'-{4-[(4-methylpiperazin-1-yl)methyl]phenyl}urea; and N-(4-{methyl[2-({4-[(methylsulfonyl)methyl]phenyl}amino)pyrimidin-4-yl]amino}phenyl)-N'-{4-[(4-methylpiperazin-1-yl)carbonyl]phenyl}urea;

or a salt, thereof.

14. A pharmaceutical composition, comprising: a therapeutically effective amount of a compound as claimed in claim 1, or a salt, thereof and one or more of pharmaceutically acceptable carriers, diluents and excipients.

15. The pharmaceutical composition of claim 14, further comprising at least one additional anti-neoplastic agent.

16. The pharmaceutical composition of claim 14, further comprising an additional agent which inhibits angiogenesis.

17. A pharmaceutical composition, comprising: a therapeutically effective amount of a compound as claimed in claim 2, or a salt thereof and one or more of pharmaceutically acceptable carriers, diluents and excipients.

18. The pharmaceutical composition of claim 17, further comprising at least one additional anti-neoplastic agent.

19. The pharmaceutical composition of claim 17, further comprising an additional agent which inhibits angiogenesis.

20. A pharmaceutical composition, comprising: a therapeutically effective amount of a compound as claimed in claim 13, or a salt thereof and one or more of pharmaceutically acceptable carriers, diluents and excipients.

21. The pharmaceutical composition of claim 20, further comprising at least one additional anti-neoplastic agent.

22. The pharmaceutical composition of claim 20, further comprising an additional agent which inhibits angiogenesis.

* * * * *